US006312910B1

(12) United States Patent
Vellinger et al.

(10) Patent No.: US 6,312,910 B1
(45) Date of Patent: Nov. 6, 2001

(54) MULTISTAGE ELECTROMAGNETIC SEPARATOR FOR PURIFYING CELLS, CHEMICALS AND PROTEIN STRUCTURES

(75) Inventors: John Vellinger, Floyd Knobs; Paul W. Todd; Ken Barton, both of Greenville, all of IN (US); Scott Dunn, Pendleton, KY (US); Mark S. Deuser, Floyd Knobs, IN (US)

(73) Assignee: SHOT, Inc., Greenville, IN (US)

( * ) Notice: Subject to any disclaimer, the term of this patent is extended or adjusted under 35 U.S.C. 154(b) by 0 days.

(21) Appl. No.: 09/546,075

(22) Filed: Apr. 10, 2000

Related U.S. Application Data

(60) Provisional application No. 60/128,627, filed on Apr. 9, 1999.

(51) Int. Cl.[7] ................................................. C12Q 1/68
(52) U.S. Cl. ............................ 435/6; 436/526; 210/695; 210/222
(58) Field of Search ................................ 435/6; 210/695, 210/222; 436/526

(56) References Cited

U.S. PATENT DOCUMENTS

| | | |
|---|---|---|
| 4,209,394 | 6/1980 | Kelland . |
| 4,432,873 | 2/1984 | Schuster . |
| 4,710,472 | 12/1987 | Saur et al. . |
| 4,795,698 | 1/1989 | Owen et al. . |
| 4,988,618 | 1/1991 | Li et al. . |
| 5,053,344 | 10/1991 | Zborowski et al. . |
| 5,466,574 | 11/1995 | Liberti et al. . |
| 5,541,072 | 7/1996 | Wang et al. . |
| 5,543,289 | 8/1996 | Miltenyi . |
| 5,559,002 | 9/1996 | Uzan et al. . |
| 5,681,478 | 10/1997 | Lea et al. . |
| 5,691,208 | 11/1997 | Miltenyi et al. . |
| 5,705,402 | 1/1998 | Leland et al. . |
| 5,746,321 | 5/1998 | Hettinger, Jr. et al. . |
| 5,858,223 | 1/1999 | Stadtmuller et al. . |
| 5,968,820 | 10/1999 | Zborowski et al. . |
| 5,974,901 | 11/1999 | Zborowski et al. . |

OTHER PUBLICATIONS

Zborowski, M., L.M. Moore, L. Sun and J. Chalmers (1997) Magetophoresis I. Detection of magnetically labeled cells. J. Clin. Lab. Anal. 8, 400–406.

Powers, F.J. C.a.Heath, E. D. Ball, J. Vredenburgh and A. O. Converse (1994) Separation of small–cell lung cancer cells from bone marrow using immunomagnetic beads. In Cell Separation Science and Technology, Ed. D. S. Kompala and P. Todd, American Chemical Society, Washington, pp. 256–267.

Reddy, S. L.R. Moore, L. Sun, M. Zborowski and J.J. Chalmers (1995) Determination of the magnetic susceptibility of labeled particles by video imaging. In Chemical Engineering Science, vol. 51, 6, pp 967–956. Feb. 26, 1996.

*Primary Examiner*—James Ketter
(74) *Attorney, Agent, or Firm*—Carrithers Law Office; David W. Carrithers

(57) ABSTRACT

A multistage electromagnetic separator is designed to separate magnetically susceptible materials suspended in fluids. The apparatus includes an upper plate and a lower plate set to a fill position and the fluid samples are filled into upper and lower cuvettes. The upper cuvette rotates into position above the lower cuvette aligning the upper and lower cuvettes. A translating electromagnet energizes to a programmed current level and translates from the bottom of the lower cuvette to the interface of the plates. The translating electromagnet is de-energized, and a holding electromagnet is energized to a programmed current level pulling particles within a specified mobility range into the top of the captured upper collection cuvette. The holding electromagnet is de-energized leaving the permanent holding magnet to keep the collected sample particles in the top cuvette while the upper plate rotates thereby capturing the sample of the collected particles. The process can be preprogrammed to vary or remain the same for a plurality of capture cuvettes.

The apparatus and method of use provides a method for quantitatively separating cells, proteins, or other particles, using multistage, magnetically, electromagnetically assisted separation technology.

108 Claims, 24 Drawing Sheets

QUADRUPOLE DESIGN        HEXAPOLE DESIGN

MULTISTAGE ELECTROMAGNETIC SEPARATOR FOR PURIFYING CELLS, CHEMICALS AND PROTEIN STRUCTURES

This application claims priority from U.S. Provisional application Ser. No. 60,128,627 filed on Apr. 9, 1999 and incorporated herein by reference.

This application is part of a government project, Contract No. NAS9-97027.

TECHNICAL FIELD

1. Field of the Invention

This invention relates an innovative method for quantitatively separating cells, chemicals, proteins, and other ligands, or other particles, using multistage, magnetically assisted separation technology, ("MAGSEP"). MAGSEP is extremely well suited to immunological research and analysis, pharmaceutical delivery, research and processing and other biomedical applications. Cell separation problems associated with clinical, animal, and plant research can be address using MAGSEP technology.

2. Description of the Prior Art

Almost all prior art in this field can be classified as magnetic filtration, that is, non-magnetic particles are separated from magnetic particles irrespective of their degree of magnetization. For example, Miltenyi et al., teaches that cells labeled with magnetic particles (paramagnetic, superparamagnetic or ferromagnetic) are trapped in a static tube or a flowing channel by a strong magnetic field gradient that causes them to be attracted to said tube or channel wall. Non-magnetic particles are sedimented or convected away, leaving magnetic particles captive until released from the field and collected at a later time. In U.S. Pat. No. 5,053,344, Zborowsky applies the term "magnetapheresis"—magnetic stopping, to a similar process. Liberti et al., in U.S. Pat. No. 4,795,698 teach that thin ferromagnetic pole pieces extending into a suspension of magnetic particles will attract them, and only the magnetic particles, to said pole pieces; non-magnetic particles are convected or sedimented away, the field is switched off releasing the trapped particles into suspension where they are collected as purified cells. In a chromatography-like approach, Ugelstad teaches that high field gradients can be established around beaded ferromagnetic media and fibres, thereby trapping cells labeled with magnetic particles. Other embodiments of these magnetic filtration devices have been patented previously as set forth in U.S. Pat. Nos. 4,795,698 and 5,053,344. All of these teach a similar, simple binary separation of magnetic from non-magnetic particles, and they utilize high-gradient magnetic fields.

Prior art that is closer to the field of the invention has been presented by Powers et al., who teach that a low-gradient magnetic field applied to a horizontally flowing suspension in a channel can trap magnetically labeled cells dynamically and hence potentially according to their level of magnetization by the adsorption of magnetic particles. This method has only been applied to binary separations, however. Winoto-Morbach et al. introduced the concept of "magnetophoretic mobility" implying an intrinsic parameter whereby particles could be separated according to their speed of migration in a magnetic field gradient. Mobility is the ratio of the velocity to the driving force. In an embodiment that exploits this concept, Zborowsky et al. in U.S. Pat. No. 5,968,820, measured magnetophoretic mobilities and in U.S. Pat. No. 5,974,901 teaches that a controlled laminar flow of a suspension of particles between large permanent magnet pole pieces results in the deflection of particles according to their magnetophoretic mobility. Said deflection can be exploited as a means of recovering particles according to their mobilities, or degree of magnetization. Reddy, et. al. (1995) and Zborowski, et al. (1995) have developed analytical methods for directly evaluating the magnetization of different magnetic particle types.

Competing alternative preparativetechnologies consist of different types of separation processes, including electrophoresis and centrifugation. Electrophoresis involves separating materials by passing them through an electric field with separation occurring based on the attractions of the cells to one particular charge, whether positive or negative. Many of the manufacturers in this market are dedicated solely to the manufacturing of electrophoresis equipment. A centrifuge separates cells and other materials by inertial force. Heavier material is forced outward while lighter material remains on the top of the solution. This process may be beneficial when the cells separated can handle that kind of force and are able to separate based solely on size and/or density. This technique can be especially damaging to a cell, due to the high forces imposed when the unit propels cells into a container wall.

In U.S. Pat. No. 5,974,901, Zborowski et al. teach a method in which a nearly constant force field, e.g. magnetic, is applied in a region that contains cells that are caused to migrate in the force field. By capturing a series of microscope images in the force field, particle (cell) velocities can be measured and, through software, a histogram of velocities that indicate the degree of magnetization of the particles can be produced when the force field is a magnetic force field. One application of this method is the measurement of magnetophoretic mobility, the ratio of particle velocity to the applied force field, from which additional physical and chemical information about the particle can be derived. The present invention is distinguished from the Zborowski et al reference in that while Zborowski analyzes particles on the basis of a distribution of magnetic properties, the instant invention provides a means to capture them on the basis of said properties, collecting and separating particles on the basis of their magnetophoretic mobility and is not limited to the collection of merely analytical data as taught by the Zborowski reference.

In U.S. Pat. No. 5,968,820, Zborowski et al. teach a method in which a mixture of biological cells upon whose surface is affixed a number of magnetic particles in proportion to the number of receptors of interest to the researcher can be separated on that basis in a flowing stream in which they are suspended. The flowing stream flows between two magnet pole pieces, and cells within said stream are deflected toward the pole pieces at a velocity that depends on their magnetophoretic mobility and hence magnetic susceptibility and hence receptor density. The separated cells or particles are finally collected utilizing multiple outlets in fractions with each fraction containing cells having a specified range of receptor densities. Contrary to the teachings of Zborowski et al., the instant invention uses a static feed sample in a cuvette and, through the application of magnetic force, causes cells or particles to emerge from said feed cuvette with a velocity that is proportional to magnetophoretic mobility and hence magnetic susceptibility and hence receptor density.

In U.S. Pat. No. 5,053,344, Zborowski et al. teaches a system consisting of a gap between two magnetic pole pieces in which a suspension of particles is caused to flow through a thin chamber with parallel walls by gravity or some other driving means,.The chamber is positioned so as to allow the particles suspended in the flowing stream to experience a spatially graded magnetic force. The spatially graded magnetic force causes the capture of particles spatially distributed on a plane according to their magnetic susceptibility in a process traditionally termed "ferrography". Subsequent to capture, some particles, especially biological cells, can be examined according to the position at which they were captured and classified, but not collected in suspension according to magnetic susceptibility and hence, if labeled with liganded magnetic particles, receptor density. This system does not separate particles collectible in suspension and therein differs from the instant invention, which is designed to accomplish such separation and collection.

Improved techniques for separating living cells and proteins are increasingly important to biotechnology because separation is frequently the limiting factor for many biological processes. In response to that need, the present invention was developed to provide a method for quantitatively separating cells, particles, ligands, proteins, and other chemcial species using a magnetic and/or an electromagnetically-assisted separation process.

SUMMARY OF THE INVENTION

The instant apparatus and method of use provides an innovative method for quantitatively separating cells, proteins, or other particles, using multistage, magnetically and/or electromagnetically assisted separation technology ("MAGSEP"). The MAGSEP technology provides a separation technology applicable to medical, chemical, cell biology, and biotechnology processes. Moreover, the instant invention relates to a method for separating and isolating mixtures of combinatorially synthesized molecules such that a variety of products are prepared, in groups, possessing diversity in size, length, (molecular weight), and structural elements. These are then analyzed for the ability to bind specifically to an antibody, receptor, or other ligate. Such a collection may provide a ligand library containing specific ligands for any ligate even though there are a greater number of conformations available to any one sequence. This technology provides a cell biologists a tool for studying molecular recognition. Combinational chemical libraries containing known and random sequences can be surveyed for strong ligands. Such a tool provides a means of recognizing and isolating agonists, antagonists, enzyme inhibitors, virus blockers, antigens, and other pharmaceuticals.

In clinical applications utilizing a single or multistage magnetic and/or electromagnetic separator, cells that are labeled with decreasing numbers of paramagnetic beads are separated quantitatively on the basis of the extent of labeling by using magnetic fields of increasing strength. Cells with greater numbers of magnetic beads attached to their receptors will be attracted to a weak magnetic field, while cells with fewer beads will not as shown best in FIG. 1. This principle establishes the basis for separating ("classifying") cells or other particles according to their magnetic strength, using either a rate or an equilibrium process.

One main reason that electromagnetic field-assisted methods have not been heavily employed commercially in the past is the mystique of equipment used in the field. The physics is considered too complex, but it is rather simple in fact. There is further misunderstanding about the mechanism of separation. In addition to the existence of a mystique, real physical factors also have been a deterrent to magnetic field-assisted separations. Most magnetically assisted separations that require the specific adsorption of beaded media to the separand also require some kind of flowing device for removing unwanted particles.

The multistage electromagnetic separator of the instant invention overcomes these barriers by greatly simplifying the electromagnetic field-assisted separation process. The separator does not require a stabilized matrix such as gel, paper, or density gradient. The technology does not require any forced flow of fluid for magnetic separation. The iterative transfer of fluids minimizes flows and provides a milder and more suitable environment for separating and purifying cells and proteins. The electromagnetic separator technology incorporated into the present invention also offers automatic decanting of contaminant suspensions. The unwanted cells or particles are simply left behind as by-products of the process in an opposing half chamber. Finally, the end-user of the apparatus will appreciate the added efficiency of needing to make only one buffer to complete extraction and to collect automatically separated fractions without the complications of pumping and volume measurements.

Another application of magnetic separation technology that is in its infancy is the development of neoglycoconjugates. Many cells, enzymes, and lectins possess recognition sites for specific carbohydrates ("lectin" means "carbohydrate binding protein") By conjugating specific carbohydrates (oligo- or polysaccharides) to the surface of magnetic beads, specific cells, enzymes or lectins can be isolated by HMGS or MACS. This represents an ideal application for MAGSEP, since different glycoconjugates can be linked to magnetic beads of different strengths, thus separating, out of a mixed population, cells that recognize glycoconjugate A on strongly magnetizable beads from those that recognize glycoconjugate B on weakly magnetizable beads. Furthermore, MAGSEP could also cause the collection of bead-free cells at the end of the separation by adding a solution of free sugars that competed for the magnetic binding sitesthreby setting the magnetically captured cells free.

In addition to the above very recent innovation, needs for the separation of cells on the basis of receptor density have been identified. Research laboratories have recently used receptor number as a dependent variable in a variety of scientific applications. In endocrinology mouse leukemia cells exhibit reduced beta-adrenergic receptors, in growth regulation the number of EGF receptors is regulated by cell density in cultures which can be modulated by protamine, in virology the cell surface has limited numbers of receptors for herpes virus glycoprotein D which is required for virus entry into cells, in carcinogenesis the H-ras oncogene alters the number and type of EGF-beta receptors, in infectious diseases galanin receptor levels are coupled to pertussis toxin resistance of pancreatic cells, and a diphtheria toxin receptor-associated protein has been identified. In neurology regulation of opioid kappa receptors occurs in stimulated brain cell cultures, in nutrition mast cells lose IgE receptors in protein malnutrition, and vasoactive intestinal peptide (VIP) receptors have been discovered at high density. This relatively small sample of recent findings indicates clearly that tools for studying cells with modified receptor densities would be welcome.

Methods exist for utilizing high-magnetic-gradient technology for the specific removal of cells from the human circulation by labeling them with immunobead ligands. This is now practiced as a binary separation which might benefit from continuous separation afforded by the instant invention.

The use of magnetically delivered therapeutics is another potential application for magnetic particle separation technology.

Once magnetized particles or microcapsules for delivery have been made, it is necessary to separate weakly magnetized particles from those with the highest susceptibility. Since strongly magnetized particles will be required, an important consideration is the distance between the external magnet and the delivery site and the undesirability of delivering weak particles, loaded with drug, to normal-tissue sites to produce unwanted side effects. The technology may be utilized as a means for the separation of a specified subset of T-lymphocytes for transfusion of AIDS patients, or a specified subset of islet cells for the treatment of diabetes.

The counting of prepurified cells in diagnostic tests parallels developments in flow cytometry which costs up to 100 times as much. The low cost of this technology can not be overstated: AIDS care givers in the developing world are puzzled over how to do diagnostic tests that involve flow cytometry in environments that lack flow cytometers. The instant invention utilizing a multistage electromagnetic separator solves these problems and promises to offer solutions to such global health problems.

In theory, there are no capacity limits to magnetically-assisted separation. It can be small, for diagnostic purposes, or large, for preparative applications such as cell transplants. The latter is significant since a tall magnetic column, which would be required (possibly up to 1 meter and a field greater than 1–2 Teslas) for the quantitative resolution we propose, is replaced by the staged separation cavities in a rotating disk with several modest permanent magnets and electromagnets as illustrated in FIG. 2.

The development of user-friendly devices that are capable of separating particles according to quantity of ligand on their surfaces appears to be the greatest need in improving magnetically-assisted separation devices. The magnetic separation industry has made considerable progress in this regard, but the technology to date has been limited to binary separation methods. An example would be Baxter Healthcare's Isolex-300 Magnetic Cell Separator, which chooses stem/progenitor cells through use of monoclonal antibody (MAB)-coated magnetic beads. The stem cells are selected for reconstituting bone marrow damaged by chemical or radiation treatment. The instant MAGSEP invention represents a quantum leap in progress by finally providing a reliable method for differential separation on the basis of small differences in surface composition.

Most ligand-based (such as receptor-antibody) cell separation methods are binary—all or nothing. By combining magnetic attraction, used as a rate process, with countercurrent extraction, it is now possible to use magnetic separation of cells as a quantitative technique, separating on the basis of the number of ligands bound per cell. This could be qualitative, based on the amount of ligand bound to each kind of cell, or quantitative, based on the amount of ligand bound to cells of the same type, some with high receptor content and some with low.

It is an object of the present invention to provide a method for quantitatively separating cells, proteins, or other particles, using multistage, magnetically, electromagnetically assisted separation technology, ("MAGSEP").

It is an object of the instant invention to provide a method for separating and isolating mixtures of combinatorial synthesized molecules such that a variety of products are prepared, in groups, possessing diversity in size, length, (molecular weight), and structural elements which may be analyzed for the ability to bind specifically to an antibody, receptor, or other ligate, providing a means for forming a ligand library containing specific ligands for any ligate to provide a cell biologists a tool for studying molecular recognition.

It is an object of the present invention to provide a means of recognizing and isolating agonists, antagonists, enzyme inhibitors, virus blockers, antigens, and other pharmaceuticals using combinational chemical libraries containing known and random sequences.

It is a further object of the present invention to provide a method of magnetic cell and cell components sorting for plants and animals.

It is another object of the present invention to develop a plate assembly capable of incorporating at least one and preferably a multiple of magnets, electromagnetic devices, and/or combinations thereof and base support.

It is another object of the present invention to design electromagnetic hardware and drive boards capable of providing variable field strength (in the 1–1000 mT range).

It is another object of the present invention to design an indexing system for plate translation.

It is another object of the present invention to incorporate and configure the electromagnetic separator of the present invention to fit within an ADSEP containment enclosure for space flight and remote applications.

It is another object of the present invention to incorporate data management and processing control system.

It is another object of the present invention to provide an electromagnet exhibiting a relatively quick change in polarity to enhance mixing.

It is another object of the present invention to provide an electromagnetic separator having a constant force and a formed flux density.

It is an object of the present invention to provide an embodiment, whereby biological cells that have on their surfaces receptors that can be bound by an antibody can be attached to magnetic particles through specific chemical ligands such as avidin, a protein that reacts with biotin, a vitamin that can be chemically bound to the antibody thereby attaching the cells to magnetic particles to be collected by the present invention.

It is another object of the present invention to select homogeneous populations of magnetic particles from heterogeneous magnetic particle populations synthesized for use in cell research applications.

It is another object of the present invention to select strong, homogeneous populations of magnetic particles for targeted drug delivery whereby magnetic microparticles are used for the parenteral delivery of targeted drugs based wherein the differentiation and selection due to the fact that magnetically weak particles are inimical to this modality.

It is another object of the present invention to utilize an embodiment wherein the translating magnet is a permanent dipole, a permanent quadrupole, or a permanent hexapole magnet, or the magnet is a dipolar, quadrupolar or circular electromagnet.

It is another object of the present invention to utilize an embodiment wherein the translating magnet is a series of fixed electromagnets of any polarity, operated in sequence so as to sweep particles into a common starting band.

It is another object of the present invention to utilize an embodiment wherein the control of the translating magnet(s) holding magnet(s) and disk transfer system is controlled by a computer and custom software.

It is another object of the present invention to utilize an embodiment wherein capture cavities and holding magnets are arrayed in a straight line or some other geometrical relationship especially including in a circle.

It is another object of the present invention to utilize an embodiment wherein more than one sample cuvette, with their translating magnets, serve the array of capture cavities.

It is another object of the present invention to utilize an embodiment wherein the invention is used to separate magnetically labeled biological cells.

It is another object of the present invention to utilize an embodiment wherein the invention is used to select homogeneous populations of magnetic microparticles for application to cell separation and other biochemical separation processes.

It is another object of the present invention to utilize an embodiment wherein the invention is used to select homogeneous subpopulations of magnetic particles for targeted drug delivery.

It is another object of the present invention to utilize an embodiment wherein the invention is used in any process in which the desired goal is the classification (separation) of magnetic particles according to magnetophoretic mobility and hence volumetric differential susceptibility.

It is another object of the present invention to utilize an embodiment wherein no translation magnet is used.

These and other objects of the present invention will be more fully understood from the following description of the invention.

BRIEF DESCRIPTION OF THE DRAWINGS

A better understanding of the present invention will be had upon reference to the following description in conjunction with the accompanying drawings in which like numerals refer to like parts throughout the several views and wherein.

DESCRIPTION OF THE PREFERRED EMBODIMENT

The present invention is an electromagnet separator 10 for quantitatively separating substrates including cells, proteins, ligands, chemicals, antigens, and other particles by using an electromagnetically assisted separation process. The multistage electromagnet, ("MAGSEP"), 10 of the present invention allows a multiple stage separation based on magnetic susceptility and magnetophoretic mobility. The preferred embodiment of the electromagnet separator 10 is a multistage counter-current device in which the substrates or cells are labeled with decreasing numbers of paramagnetic beads and separated quantitatively on the basis of the extent of labeling by using magnetic fields of increasing strength. The electromagnetic separator 10 enhances product recovery by collecting fractions automatically and provides differential separation where only binary separations were previously possible. It will work with any aqueous suspension and has the flexibility to operate efficiently in commercial applications and space research laboratories. The invention makes it possible to separate large quantities of immunological, hematological, and other differentiating cell types in direct proportion to their surface antigen content. Moreover, it makes it possible to either refine samples to a higher level or purity of categorize portions of the sample based or magnetic susceptibility and/or magnetophoretic mobility. Moreover, the field strength can be varied to produce uniform capture of magnetized cells or other substrates.

Magnetophoretic mobility is defined as:

$$\mu_m = \frac{v_m}{B - \frac{dB}{dZ}}$$

where B is the capture magnet's magnetic field strength and $v_m$ is the velocity of the particle in the magnetic field. The velocity is a function of the magnetic field and properties of the particle and the solvent:

$$v_m = \frac{2a^2 \Delta x B dB}{a\eta \mu_o dZ}$$

Therefore, each stage in the MAGSEP device selects particles of different magnetophoretic mobilities. The particles in each of the stages will have a different mobility distribution. The low magnetic field strengths will select particles of higher mobility, whereas the higher magnetic field strengths will select for lower mobilities. Therefore, each stage will contain a magnetophoretic mobility cutoff, based on the magnetic field strength of the capture magnet, and the dwell time of the capture.

In equation (2) a is a particle radius, $\Delta X$ is the magnetic susceptibility difference between particle and medium, $\eta$ is viscosity, and $\mu$ is the magnetic permeability of free space.

Figure 1:
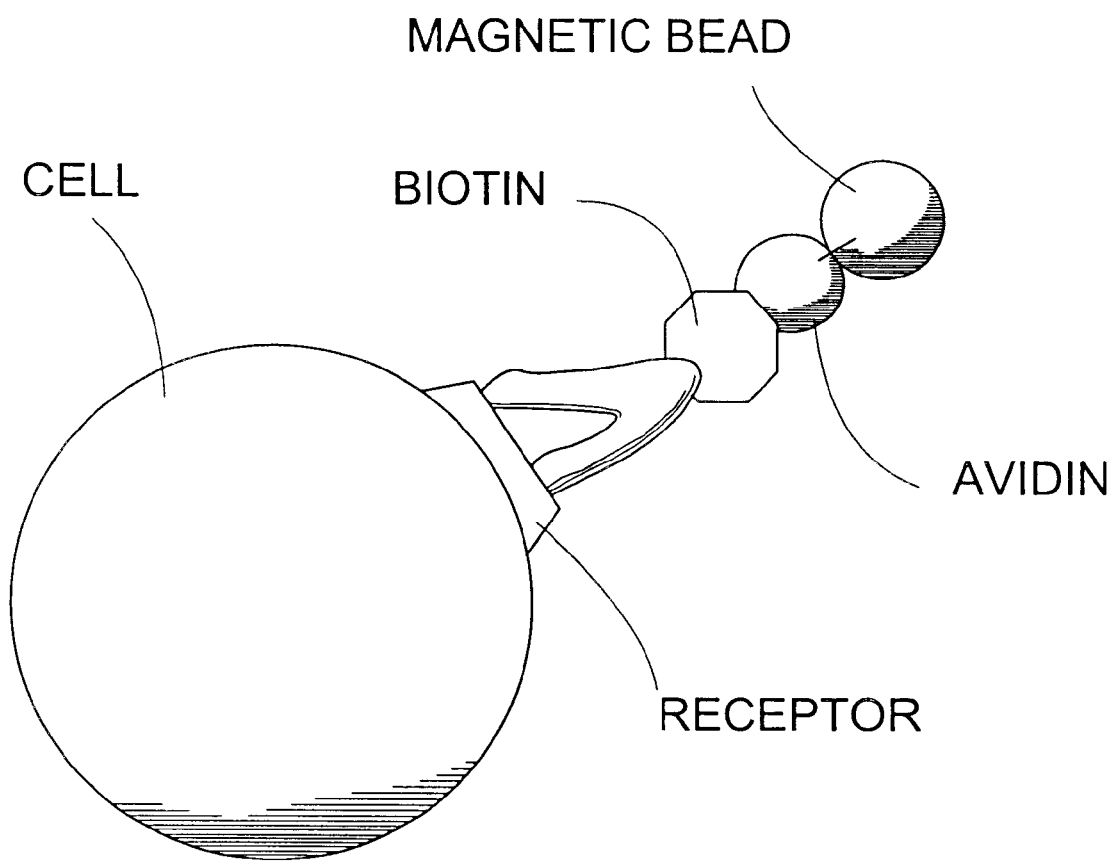
FIG. 1 is a magnetic bead attached to a cell receptor by a ligated specific antibody.

The method of cell separation using a magnetic field has been implemented as a binary separation between cells that have and have not bound magnetic micro spheres on the basis of a specific surface ligand, as best shown in FIG. 1. As shown an antigen is attached to a cell receptor site and biotin is attached to the antibody. A magnetic bead is attached to avidin which is connected to the biotin. Since biological cells that have on their surfaces receptors that can be bound by an antibody can be attached to magnetic particles through specific chemical ligands such as avidin, a protein that reacts with biotin, a ligand can be chemically bound to the antibody.

Figure 2:
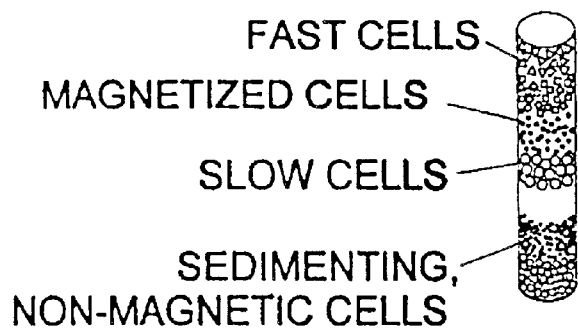
FIG. 2 is a schematic representation of a multistage electromagnetic separator showing comparison with a hypothetical magnetic chromatography column.
Figure 2:
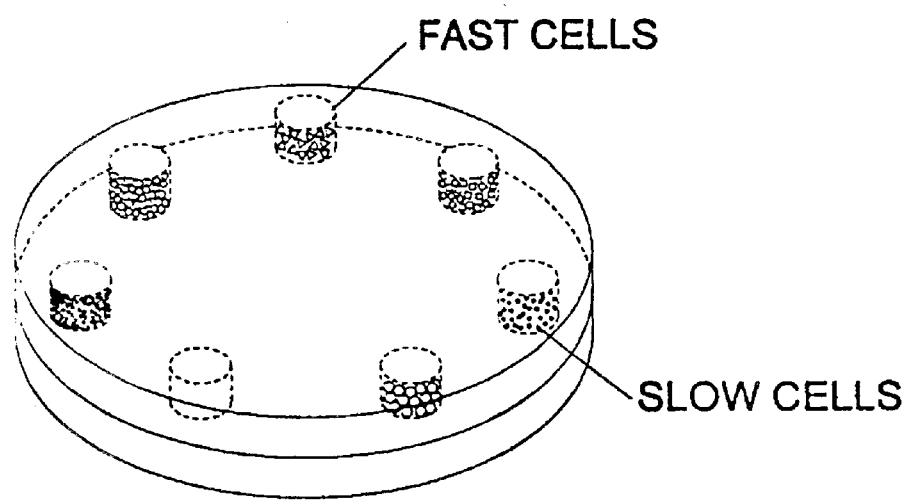

FIG. 2 is a schematic representation of a multistage electromagnetic separator showing comparison with a hypothetical magnetic chromatography column. As noted heretofore, the MAGSEP device utilizes a step-wise rotary distribution and containment system which selects, isolates, and stores particles of different magnetophoretic mobilities. The particles in each of the stages will have a different mobility distribution. The low magnetic field strengths will select particles of higher mobility, whereas the higher magnetic field strengths will select for lower mobilities. Therefore, each stage will contain a magnetophoretic mobility cutoff, based on the magnetic field strength of the capture magnet, and the dwell time of the capture. FIG. 2 demonstrates that the fast cells have the greater magnetophoretic mobility. Thus, the cells are separated according to the quantity of ligand on their surfaces.

By combining magnetic attraction, used as a rate process, with countercurrent extraction, it is possible to use magnetic separation of cells as a quantitative technique separating on the basis of the number of ligands bound per cell. This could be qualitative, based on the amount of ligand bound to each kind of cell, or quantitative, based on the amount of ligand bound to cells of the same type, some with high receptor content, and some with low receptor content.

Figure 3:
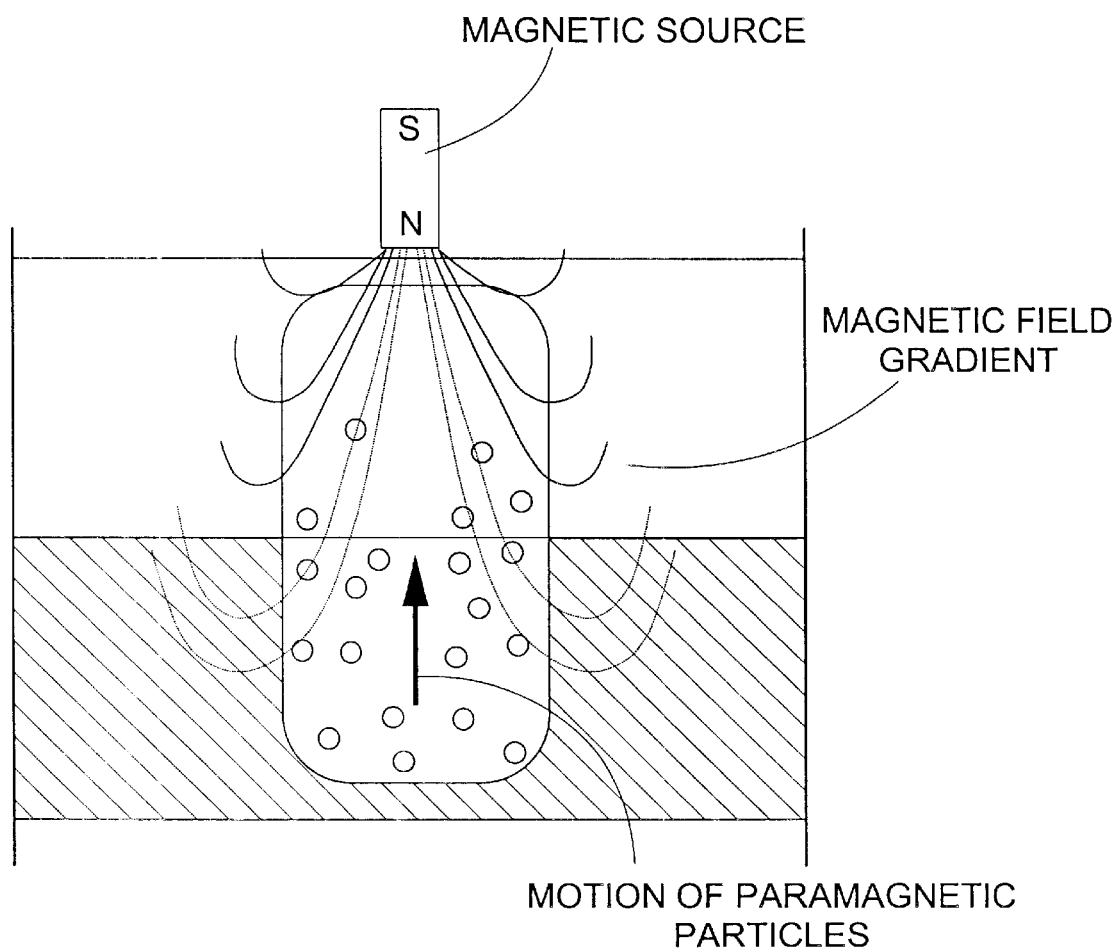
FIG. 3 is a diagram showing a single stage of the magnetic separation process wherein cells that bind magnetic beads are drawn along the gradient toward the pole.

FIG. 3 is a diagram showing a single stage of the magnetic separation process whereby cells that bind magnetic beads are drawn along the gradient toward the pole. The illustration shows a magnetic source, either permanent or electromagnetic, at the top of the container or cuvette, which produces a magnetic field gradient therein. Magnetic force creates movement of the paramagnetic particles in accordance with their magnetophoretic mobility. The electromagnetic separation device 10 of the present invention provides a very clean separation wherein the particles are loosely aligned in strata with the most magnetic particles at the top of the cuvette, particles with a lower magnetic suceptiblity are suspended in the middle, and particles with little or no magnetic susceptibility are suspended in the bottom of the cuvette.

For example, all separands attached to magnetized particles such as cells or proteins may be drawn into a half-cavity of a multistage separator from a uniform suspension, while non-magnetic separands remain distributed equally between upper and lower cavities. Nonmagnetic particles are allowed to settle for a predetermined time period. The upper cavity is moved to a position above a fresh solution that is thoroughly mixed with the separated cells. In low gravity, the result may be achieved not by sedimentation, but by dilution of non-magnetic cells out of the cavity.

The preferred embodiment achieves multi-stage separation by utilizing multiple sample cavities within the same plate assembly. The field strengths of both the translating electromagnet and the holding electromagnet can also be varied during the separation process.

Figure 4:
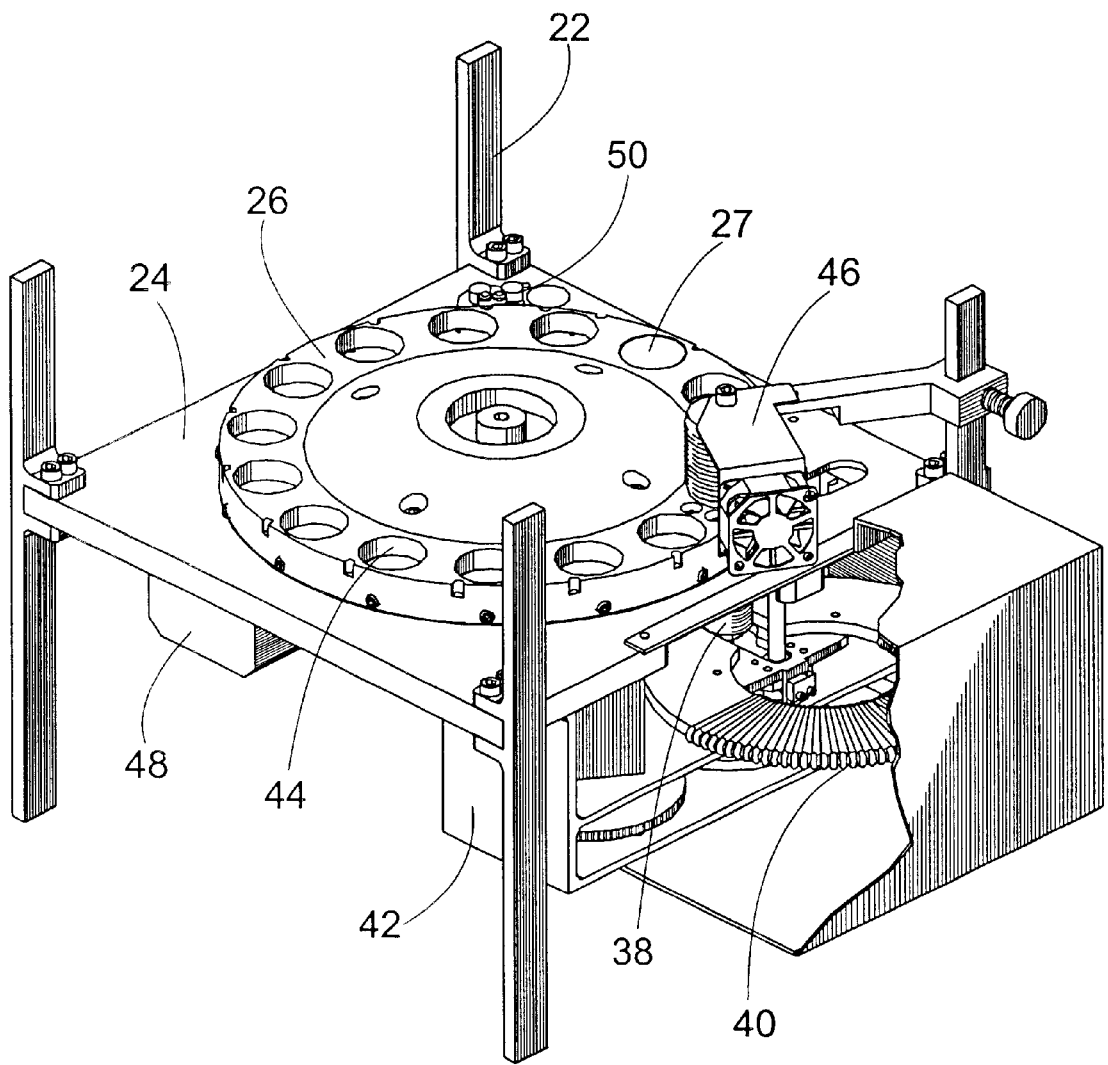
FIG. 4 is a partial cutaway view of an electromagnetic separator for sample capture showing the translating and holding magnets and associated apparatus.

FIG. 4 is a perspective view of an embodiment of a multistage electromagnetic separator 10 of the present invention. The MAGSEP unit 10 illustrates the upper plate 26 rotatively cooperatively engaging a lower plate 24 supported by a plurality of leg members 22 whereby the upper plate 26 contains at least one and preferably a plurality of upper collection cuvettes 27 in selected fluid communication with the lower plate 24 and a lower sample cuvette 38 disposed therein wherein a seal is formed thereinbetween with a sealant such as a grease, wax, or other lubricating and/or sealing constituent.

FIG. 4 also shows a translating electromagnet 40, a translation system 42, a holding magnet 44 which is a permanent magnet in the embodiment, a holding electromagnet with cooling fan 46, a plate rotation system 48, and a plate location microswitches 50.

Figure 5:
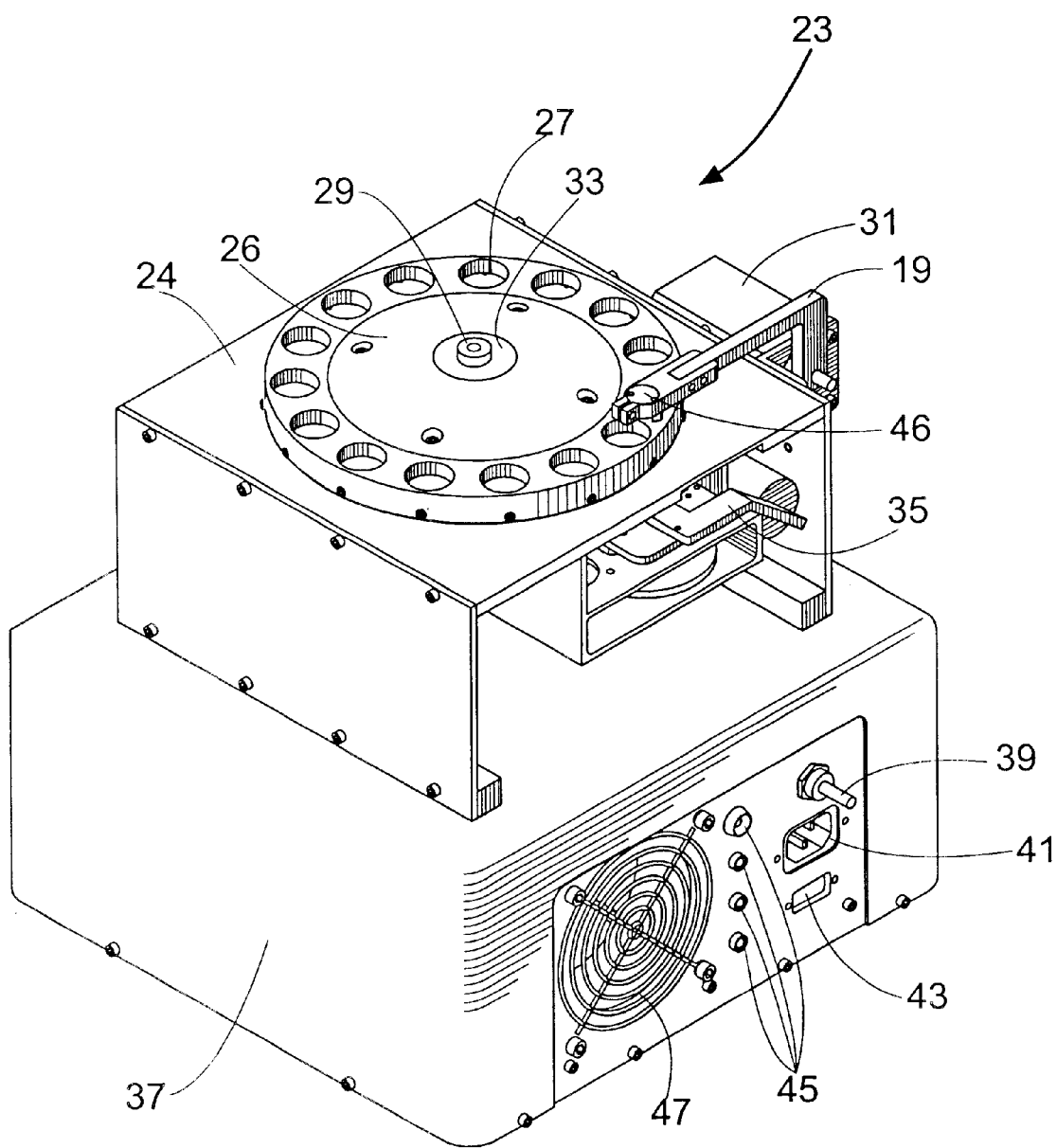
FIG. 5 is an perspective view of an electromagnet separating laboratory unit showing the plate assembly, the electromagnet assembly, the holding magnet, and base unit.

As illustrated in FIG. 5, a commercial unit is shown wherein the upper plate 26 is formed of a polymer such as a polycarbonate and is mounted onto a bearing 33 and secured with a clamping bolt 29. The legs support 22 are replaced by flanges 23 forming a base. The lower plate 24 is formed of stainless steel. A holding magnet stepper motor 31 rotates the top plate 26. The holding electromagnet 46 is suspended over the upper cuvettes 27. An electromagnet 35 is shown within the base. The base is mounted onto a housing 37 which includes a power switch 39, 110 VAC plug 41, communications port 43, indicator lights 45, and cooling fan 47.

More particularly, the laboratory unit includes a computer and software, and consists of an electronics housing and the processing unit. The electronics box has several interfaces including 110 VAC, power switch, RS 232 interface, and status lights. The unit receives power through the 110 AC connector. Power is activated with the power switch. The PC that controls the unit operates via the RS232 signal connector. The status of the power, translating electromagnet, holding magnet, and plate rotation are indicated with a graphical user interface via a personal computer.

A single processing unit consists of the upper and lower plates, plate rotation system electromagnet, electromagnet translation system, and holding magnet assembly. The plates bolt together through a tapered roller bearing that allows the plates to rotate with respect to one another The lapped interface between the plates provides a seal separating the fluids. The lower cuvette can be aligned with as many as 15 upper cuvette stations during processing. A two-phase stepping motor rotates the upper plate by driving the rotation system that engages an internal gear mounted to the underside of the upper plate. The translating electromagnet is mounted to the translation system that translates the electromagnet vertically along the lower cuvette. A programmed amount of current is sent to the electromagnet creating magnetic field across the lower cuvette. The translating electromagnet field strength can be programmed from 0 to 1400 gauss (measured at the poleface), or other selected range. The electromagnet translation system moves the electromagnet up and down the lower cuvette. The translation rates can be programmed to range from 5 micrometers/second to 2000 micrometers/second or other selected values. The holding magnet assembly consists of a permanent magnet mounted on an arm that is connect to a stepping motor. The stepping motor rotates the arm containing the holding magnet, positioning the holding magnet above the cuvette being processed.

Figure 6:
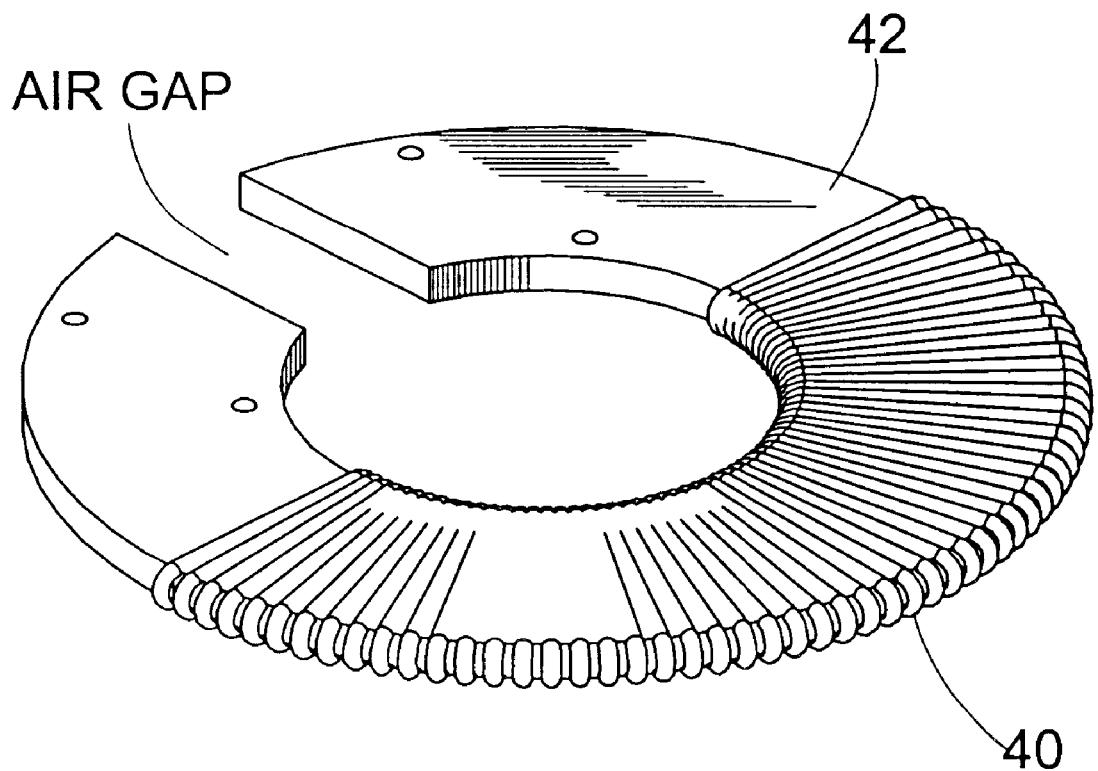
FIG. 6 is an embodiment of a translating electromagnet showing a steel core and windings.

As best shown in FIG. 6, one preferred embodiment of a translating electromagnet 40 consists of a C-1018 steel core 42 with 818 windings of 26-gage copper magnet wire formed in a disk having an air gap inbetween the distal ends thereof. It receives current ranging from 0 to 2.16 Amps from the electronics box. The magnetic field strength can be programmed from 0–1500 gauss (measured at the poleface). The electromagnetic translation system moves the electromagnet up and down the lower cuvette 28. The translation rates can be programmed to range from 120 to 250 $\mu$ms.

As best shown in FIG. 4, the holding magnet 44 assembly consists of a permanent magnet mounted on an arm 19 that is connected to a stepping motor 31. The stepping motor 31 rotates the arm 19 containing the holding magnet 44, positioning the holding magnet 44 above the upper cuvette 27 being processed.

Method of Use

MAGSEP 10 was designed to separate magnetically susceptible materials suspended in fluids. An application of the embodiment shown in FIG. 4 is as follows:

The upper plate 26 and lower plate 24 are set to the fill position (half stepped), and the fluid samples are filled into the upper 27 and lower cuvettes 28. The upper cuvette 27 rotates into position above the lower cuvette 28 aligning the upper 27 and lower cuvettes 28. The translating electromagnet 40 energizes to a programmed current level and translates from the bottom of the lower cuvette 28 to the interface of the plates 24, 26. The translating electromagnet 40 is de-energized, and the holding electromagnet 46 is energized to a programmed current level pulling particles within a specified mobility range into the top of the captured upper collection cuvette 27. Finally, the holding electromagnet 46 is de-energized leaving the permanent holding magnet 44 to keep the collected sample particles in the top cuvette 27 while the upper plate 26 rotates thereby capturing the sample of the collected particles. This process can be preprogrammed to vary or remain the same for up to 15 capture cuvettes 27.

Figure 7:
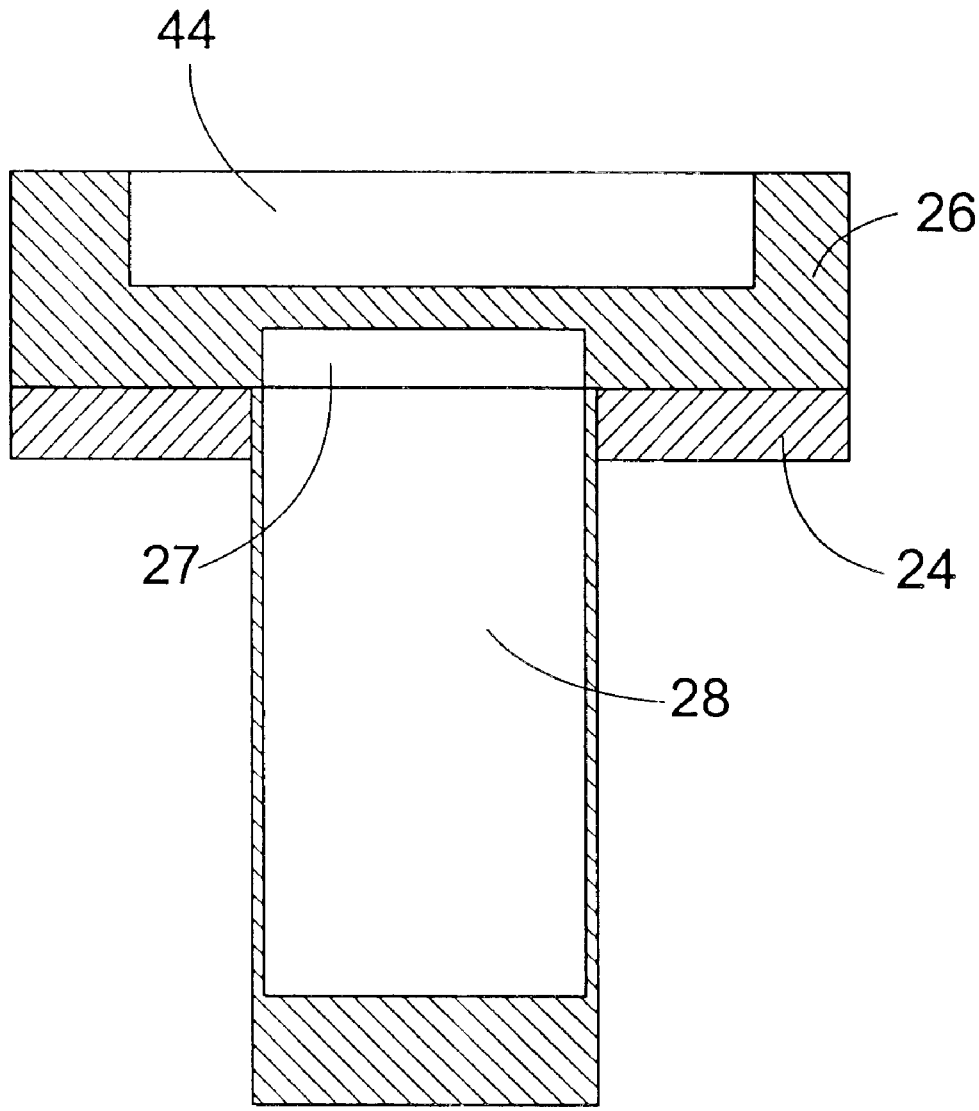
FIG. 7 shows the plate assembly used in the embodiment of FIG. 5.

FIG. 7 is a cross-section of the plate assembly showing the bottom plate 24 in cooperative engagement with the upper plate 26 in alignment with a sample cuvette 28 and an upper collection cuvette 27 and the holding magnet 44 well of the arm 19.

Figure 8:
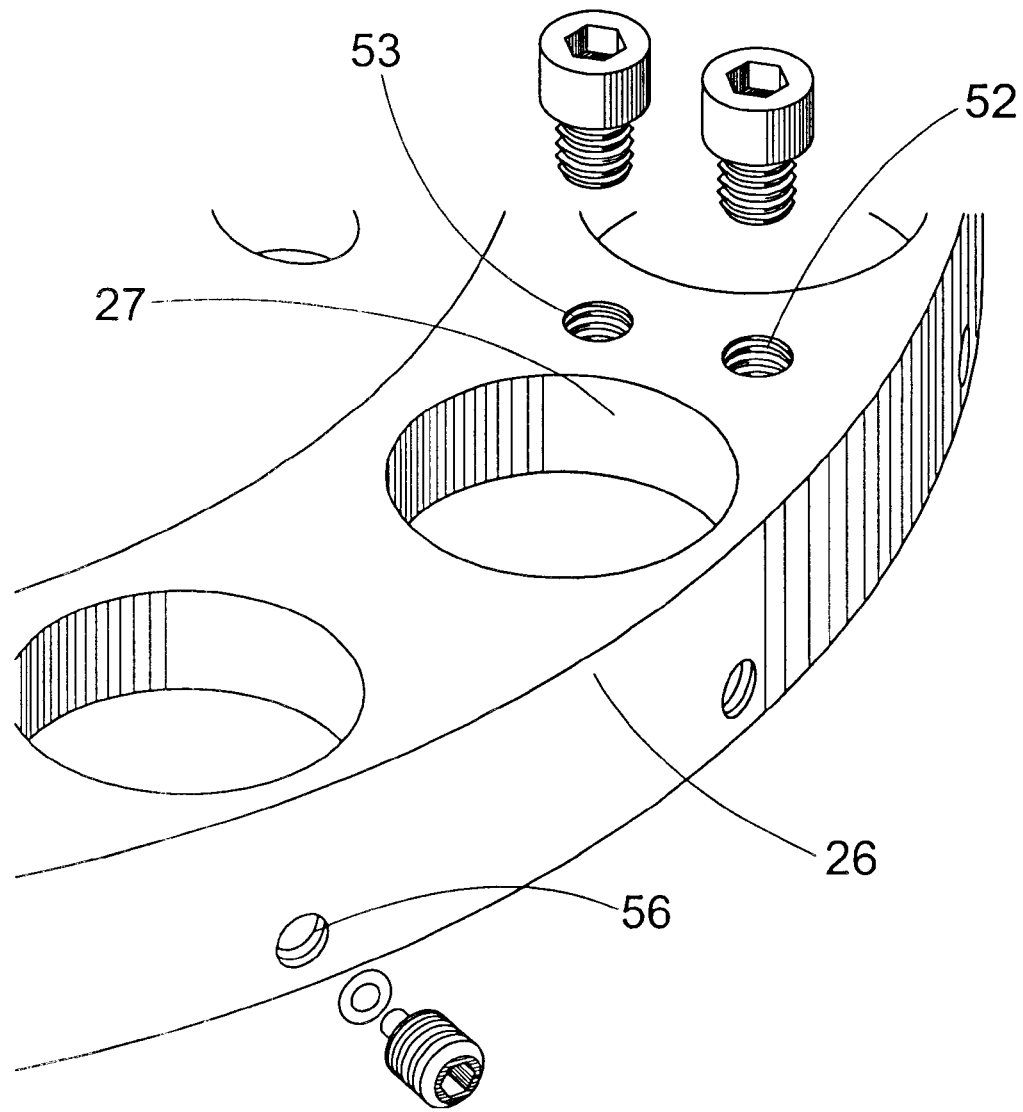
FIG. 8 is a perspective view showing the plate assembly fill ports of the embodiment of FIG. 5.
Figure 10:
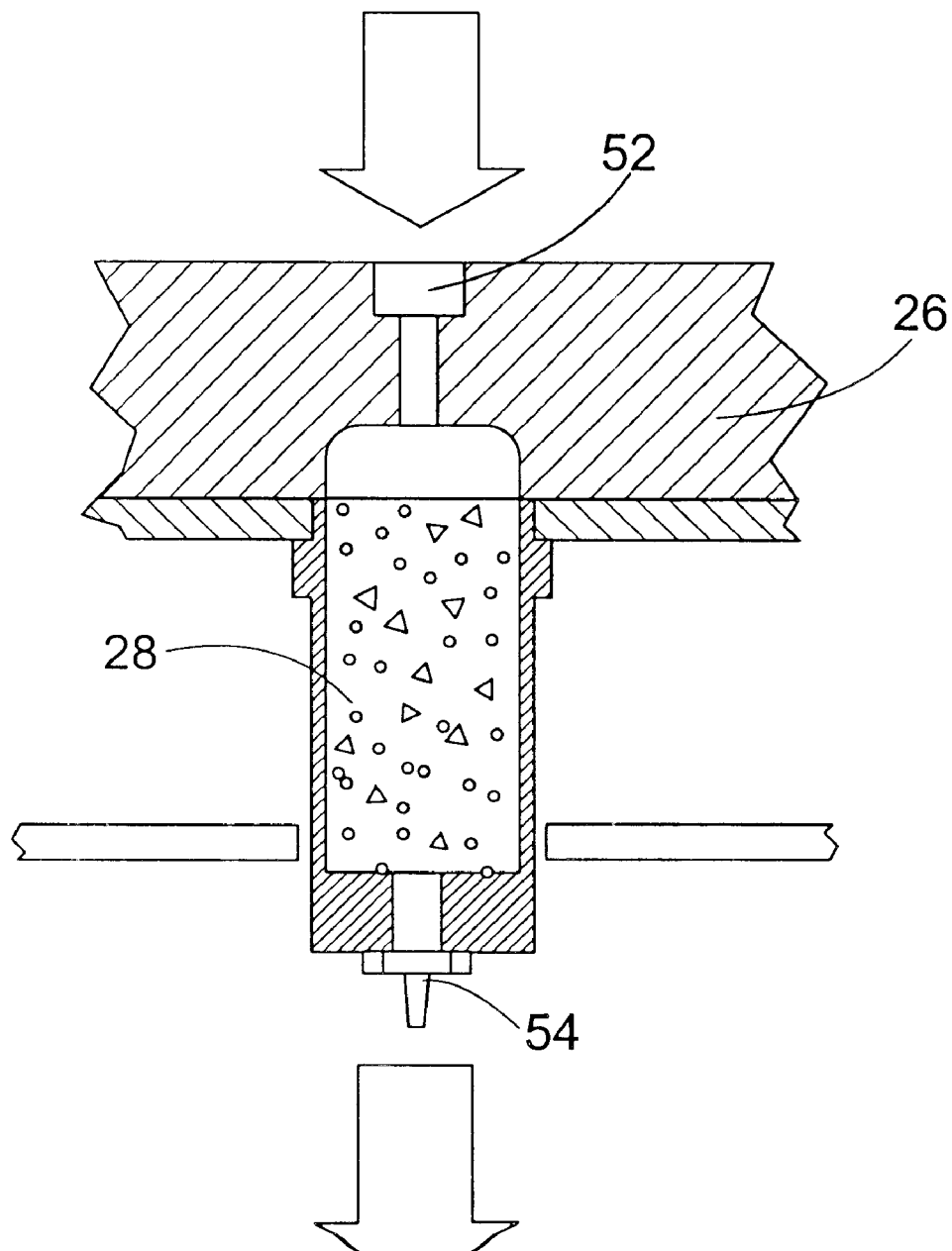
FIG. 10 is a cross-sectional view of the plate and a cuvette showing filing of the sample cuvette.

More particularly, FIG. 8 shows the filling ports within a section of a top plate 26 in fluid communication with the upper collection cuvettes 27. Also shown in FIGS. 8 and 10 is a sample fill port 52, sample vent port 53, sample drain port 54 (FIG. 10), and fill relief port 56. The plate assembly holds the samples before and after separation. The plate assembly of one preferred embodiment consists of a polycarbonate top plate, a stainless steel bottom plate, and one polycarbonate sample cuvette 28. The top plate is bolted to the bottom plate with a central clamping bolt that serves as an axle and allows the top plate to rotate with respect to the bottom plate. The top plate has at least one and preferably a plurality, 15 as shown, of cavities called collection cuvettes 27. The sample cuvette 28 is attached to an opening in the bottom plate 24. This allows the collection cuvette 27 to be rotated over the sample cuvette 28, thus allowing particles in the sample cuvette 28 to be transferred to the collection cuvette 27. The collection cuvette can then be rotated away from the sample cuvette capturing the contents of the collection cuvette. The pressure of the clamping bolt seals the top plate to the bottom plate.

FIGS. 9–14 show the step-wise progression of separating particles utilizing the present invention.

Figure 9:
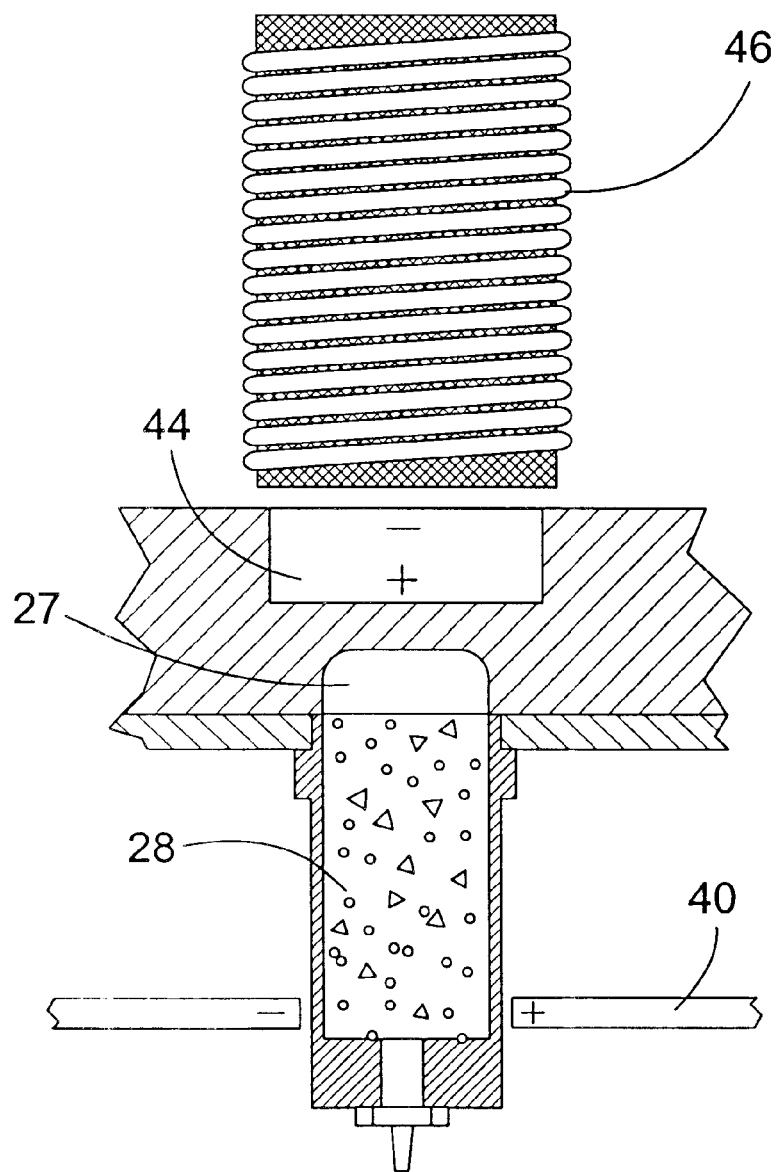
FIG. 9 is a cuvette utilized in the embodiment of FIG. 4 further showing a capture cuvette and sample cuvette together with the holding electromagnet, permanent holding magnet, and translating electromagnet.
Figure 11:
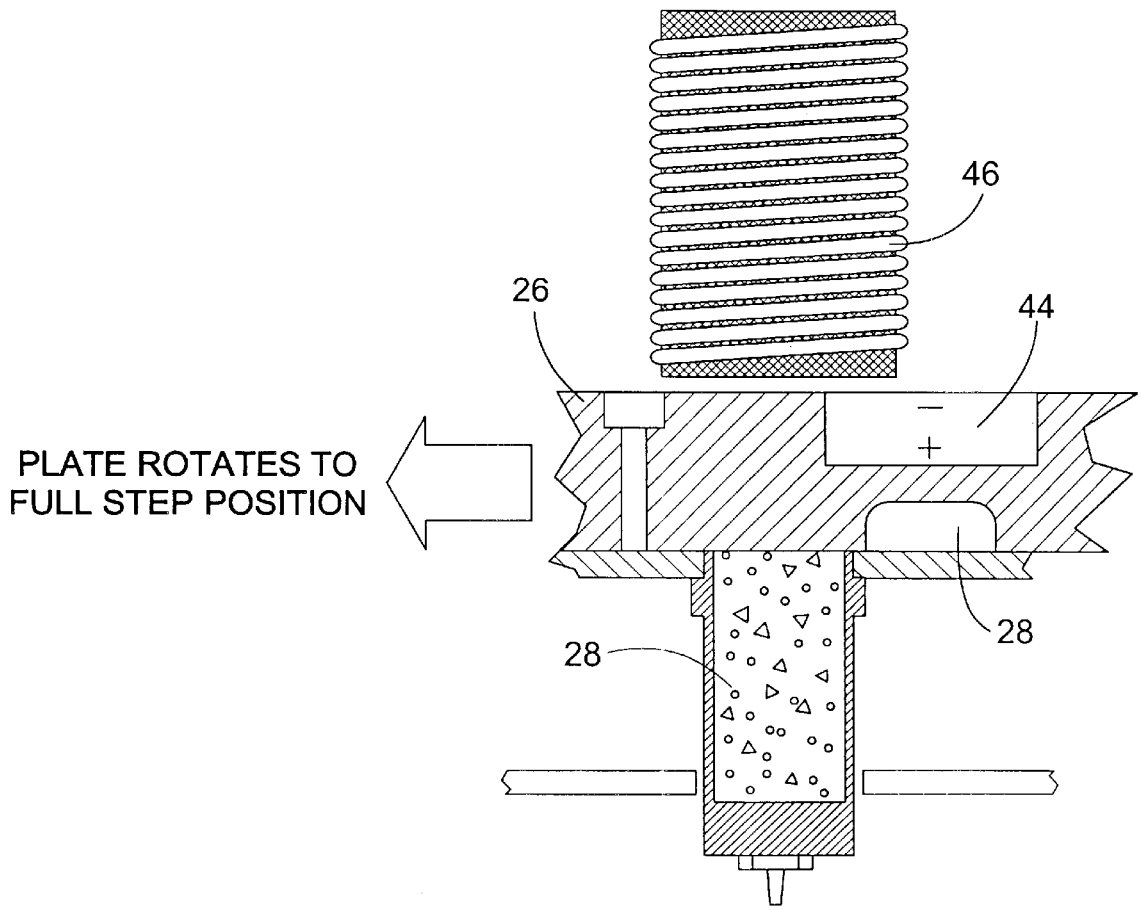
FIG. 11 is a partial cutaway view of the plate and a cuvette showing the position of the cuvette with respect to the rotation of the top plate.
Figure 12:
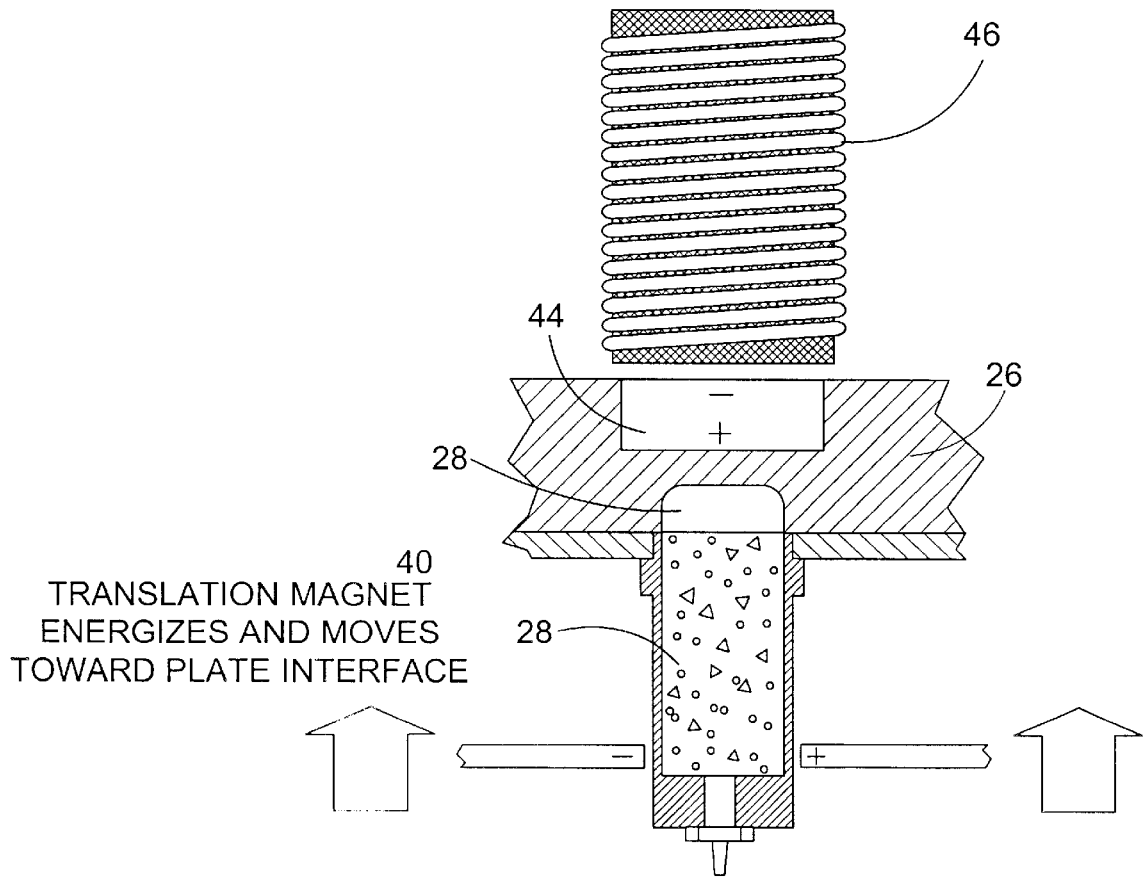
FIG. 12 is a partial cutaway view of the plate and a cuvette showing initiation of particle alignment in a sample cuvette due to the translation magnet energizing and moving particles toward the plate interface.

As shown in FIG. 9, the cuvette configuration shows the position of the capture cuvette 28, sample cuvette 38, holding electromagnet 46, permanent holding magnet 44, and translating electromagnet 40. FIG. 10 illustrates filling the sample cuvette 28 with cells or other substrate having magnetic particles selectively attached thereto. As shown in FIG. 11, the top plate 26 rotates with respect to the bottom plate 24 and the sample cuvette 28 to a full step position with sample and collection cuvettes finally aligned. The translational electromagnet 40 energizes and moves toward the plate interface as depicted in FIG. 12 showing initiation of particle alignment in the sample cuvette 28. It should be noted that the sequence for filling can be to raise the translational electromagnet 40 with the upper plate 26 one-half stepped, then bring the upper collecting cuvette 27 holding the magnet in place, or to bring the upper chamber 27 of the cuvette and magnet 40 into place, then elevate the sample cuvette 28.

Figure 13:
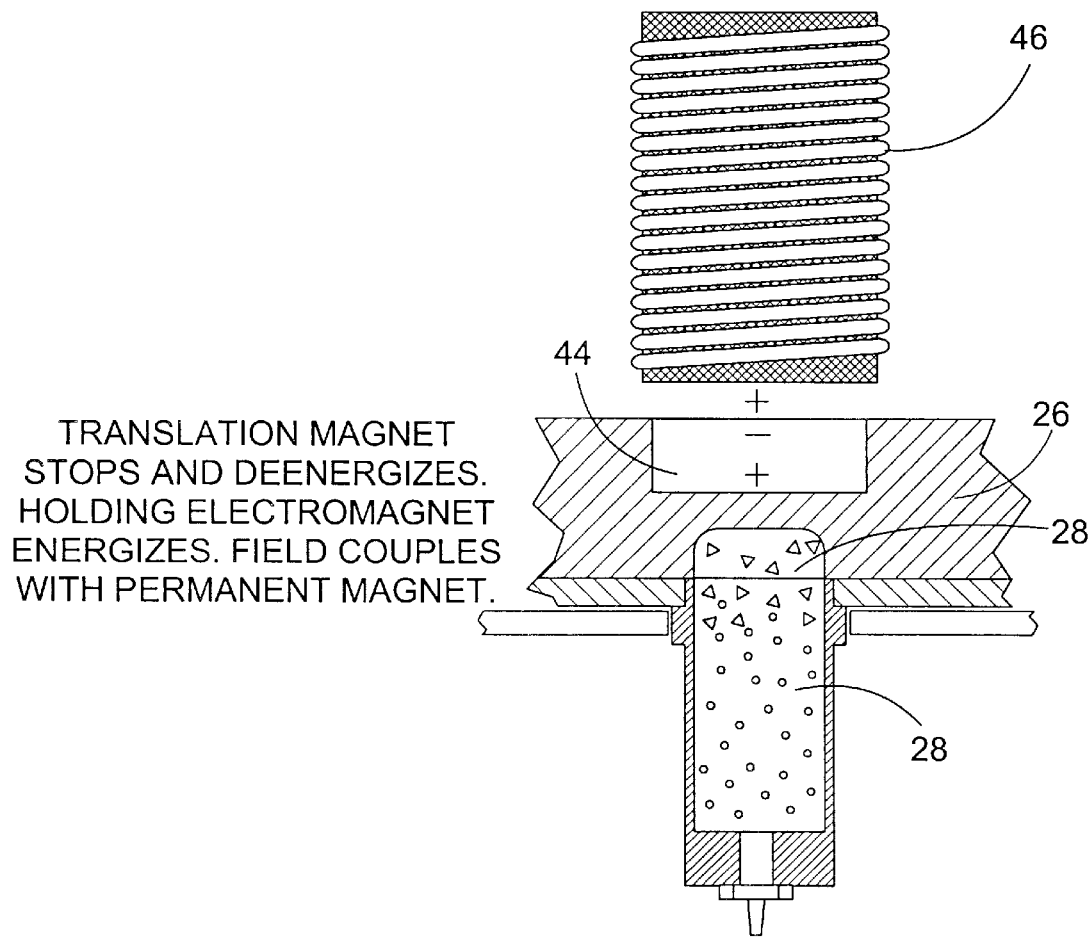
FIG. 13 is a partial cutaway view of the plate and a cuvette showing position of the translation magnet and capture of particles.
Figure 14:
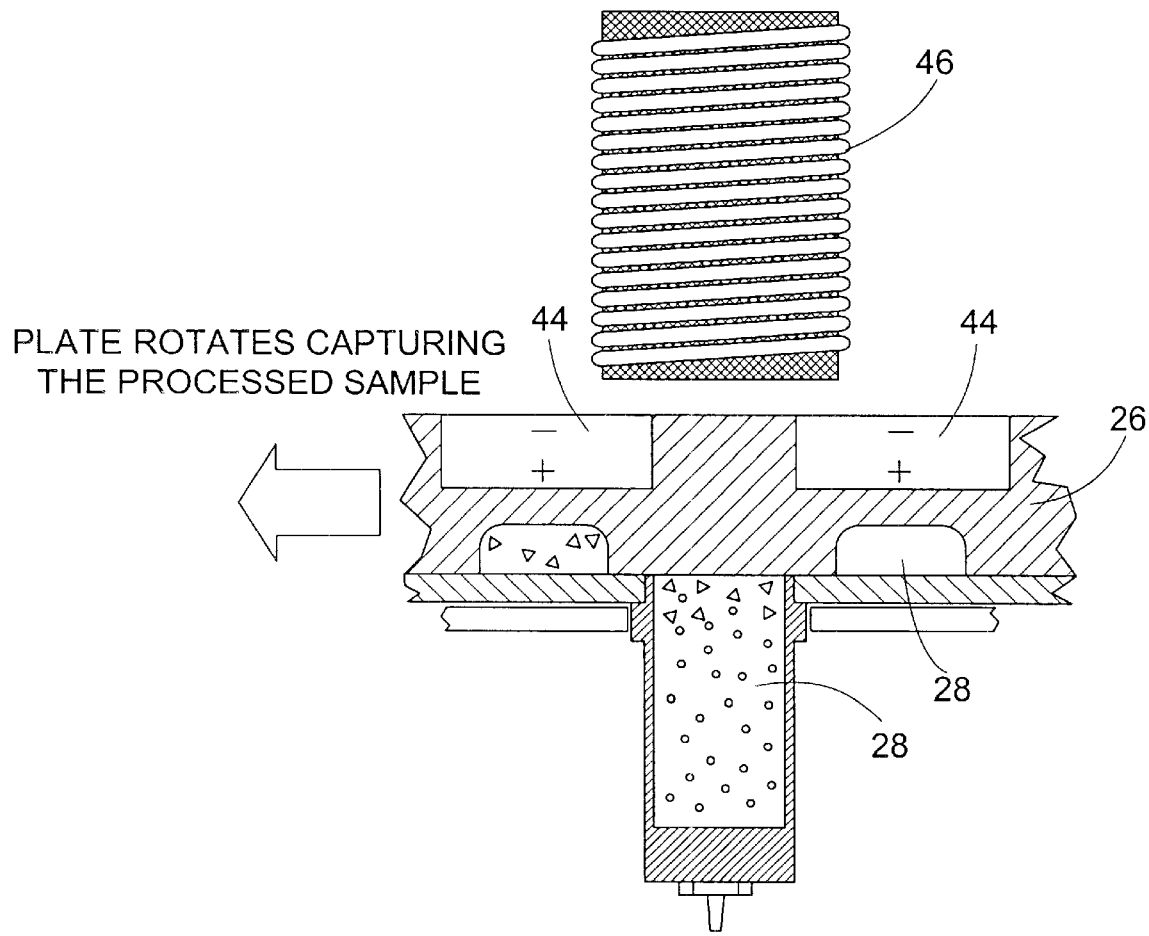
FIG. 14 is a partial cutaway view of the plate and a cuvette showing rotation of the top plate to capture a fraction of particles.

FIG. 13 shows the final position of the translating electromagnet and capture of particles wherein the translating electromagnet 40 stops and deenergizes, and the holding electromagnet 46 energizes, and field couples with the permanent magnet 44. Finally, as shown in FIG. 14, the top plate 26 is rotated to capture a selected fraction of the particles as the process sample.

Figure 15:
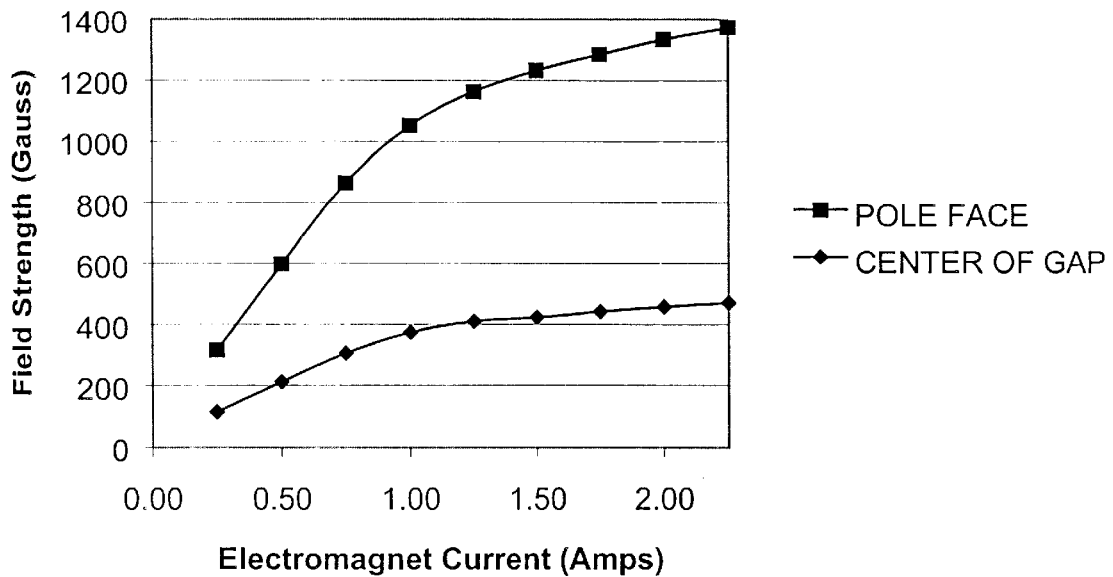
FIG. 15 is a graph showing the translating magnet field strength.

FIG. 15 is a graph depicting the translating magnet 40 field strength of an embodiment such as described in FIG. 4.

Figure 16:
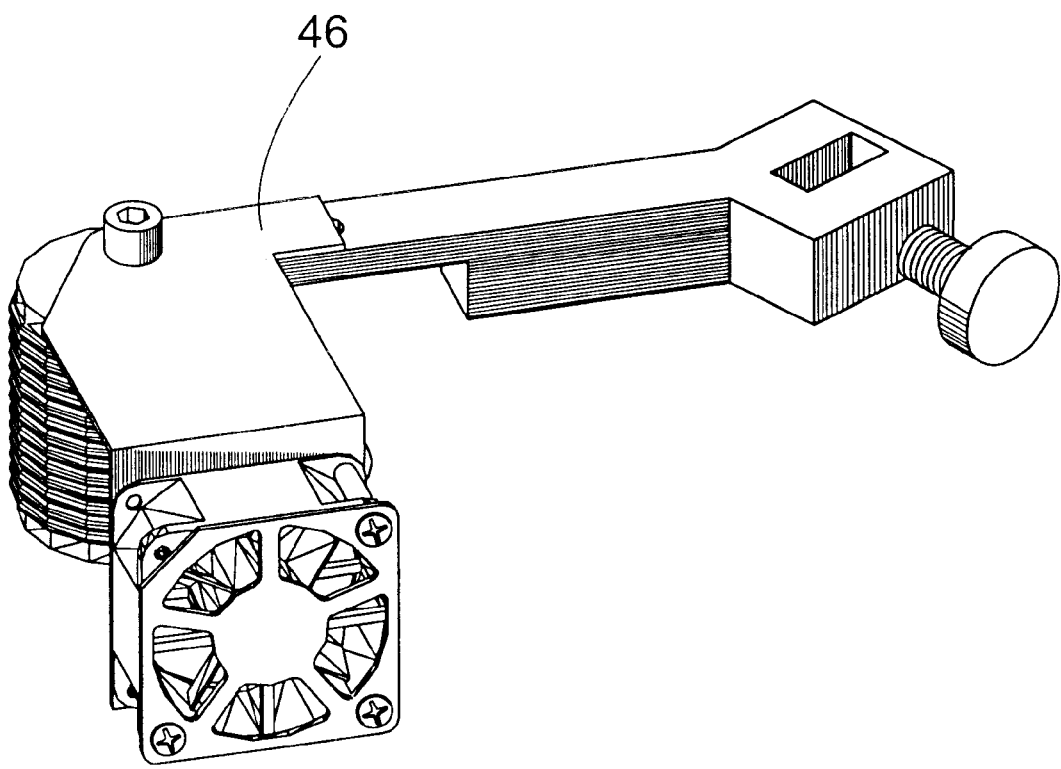
FIG. 16 shows the holding magnet assembly of the embodiment of FIG. 4.

As shown in FIG. 16, the capture or holding electromagnet 46 or programmable electromagnet is used to pull the sample past the plate interface and into the top of the upper cuvette 27.

The permanent magnet 44 is used to keep the captured sample at the top of the capture cuvette 27, preventing it from falling into the plate interface and becoming trapped between the plates 24, 26. The permanent magnet 44 size and materials can be varied to provide a variety of field strengths.

Figure 17:
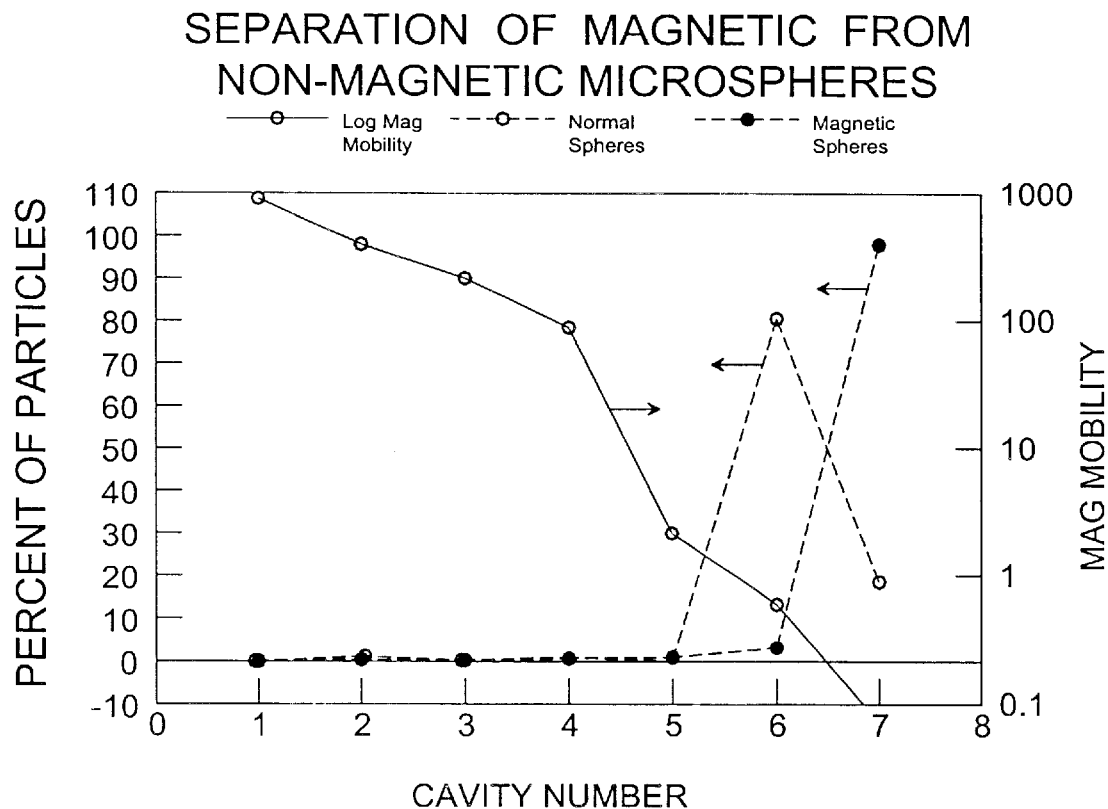
FIG. 17 shows a graph depicting the separation of magnetic from non-magnetic micro spheres.

FIG. 17 is a graph showing the results of a separation experiment separating magnetic from non-magnetic microparticles by the multistage magnetophoresis process. The experiment began with a mixture containing 90% 1–2 $\mu$m magnetic spheres ("animospheres, Polysciences, Inc.) and 10% 6.0 $\mu$m non-magnetic spheres (Interfacial Dynamics Corp.). The particles may be suspended in any type of fluid; however, water, polyethylene glycol, or ethyl alcohol are typically used. Six cavities were equipped with magnets ranging from 10 mT to 375 mT field at the pole face. Gradients were estimated using field measurements at 2.54 cm and converted to mT/m. Dwell time at each cavity was 15 min, and travel distance was on average 3 mm. From these data, a magnetophoretic mobility was estimated for each of the 7 cavities, as given on the accompanying graph.

It is seen that 80.1% of the magnetic particles were all captured in cavity #6, corresponding to a mobility of 0.6 mm/N-s, where only 2.8% of the non-magnetic particles were captured. The "purity" of the magnetic spheres went from 90% to 99.6%.

Figure 18:
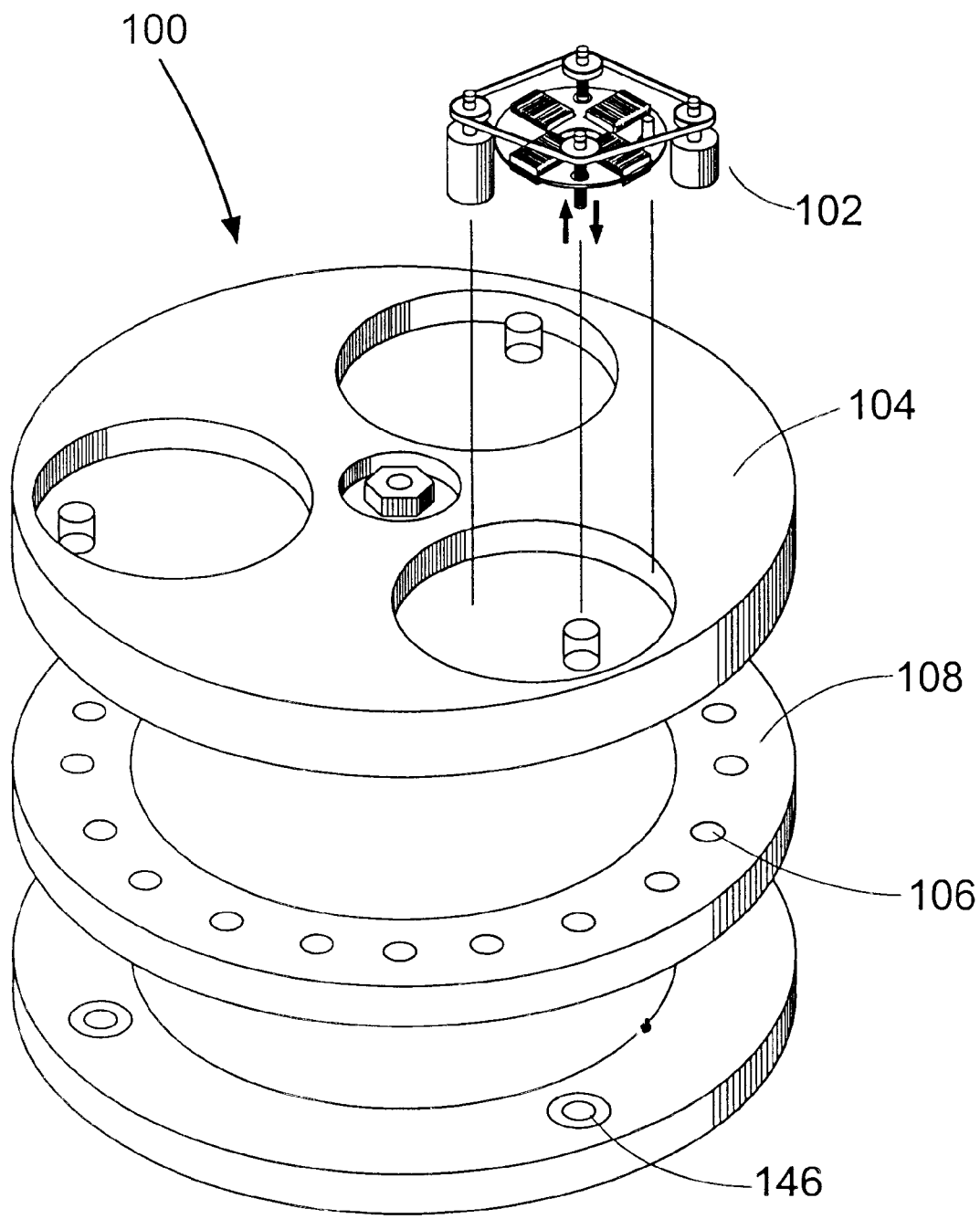
FIG. 18 is an exploded perspective view showing a plate assembly for attachment to a translating electromagnetic station.

FIG. 18 is an exploded perspective view showing an external plate assembly for a translating electromagnetic station, wherein the plate assembly 100 includes a translating electromagnetic station 102 (preferably three per sample plate 104) attached to a sample plate 104 in rotational fluid communication with a plurality of cavities 106 formed and aligned around the periphery of a collection plate 108 which is in cooperative engagement with a holding magnet (electromagnet) 146.

Figure 19:
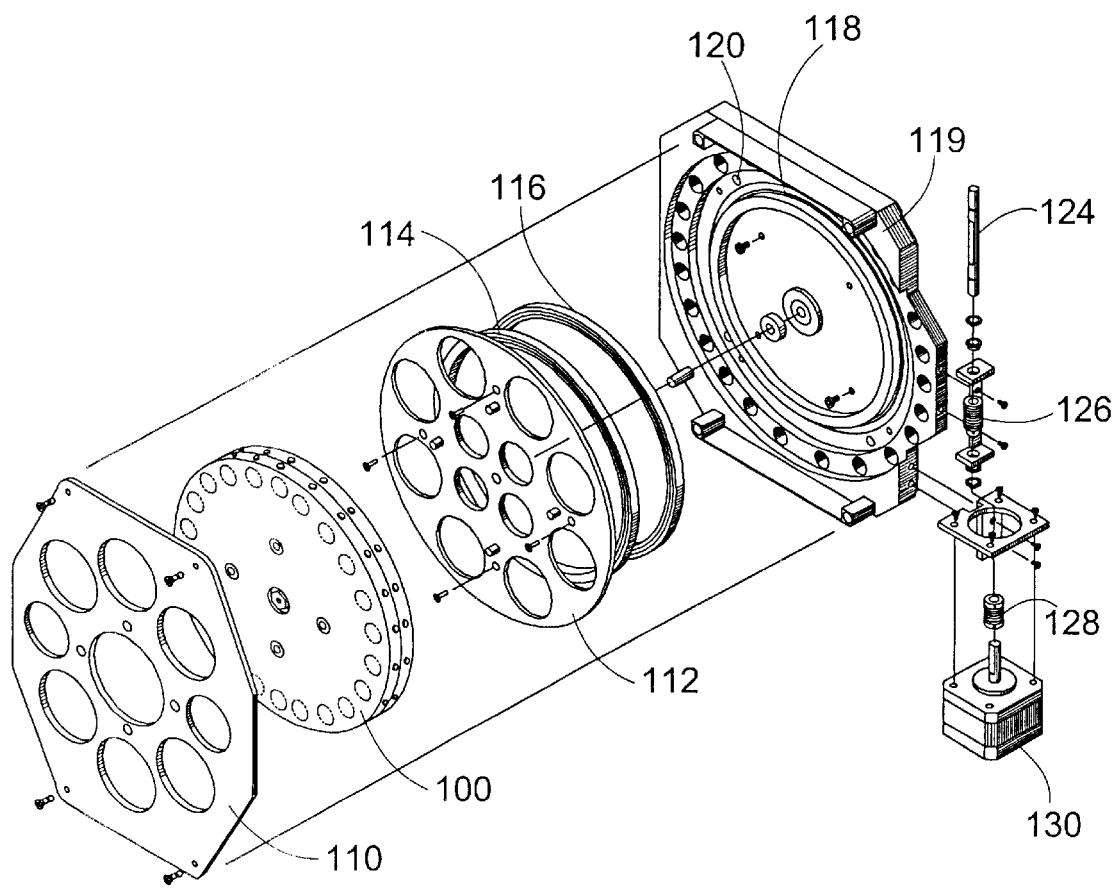
FIG. 19 is an exploded perspective view showing an indexing system for MAGSEP for rotating the collection plate.
Figure 20:
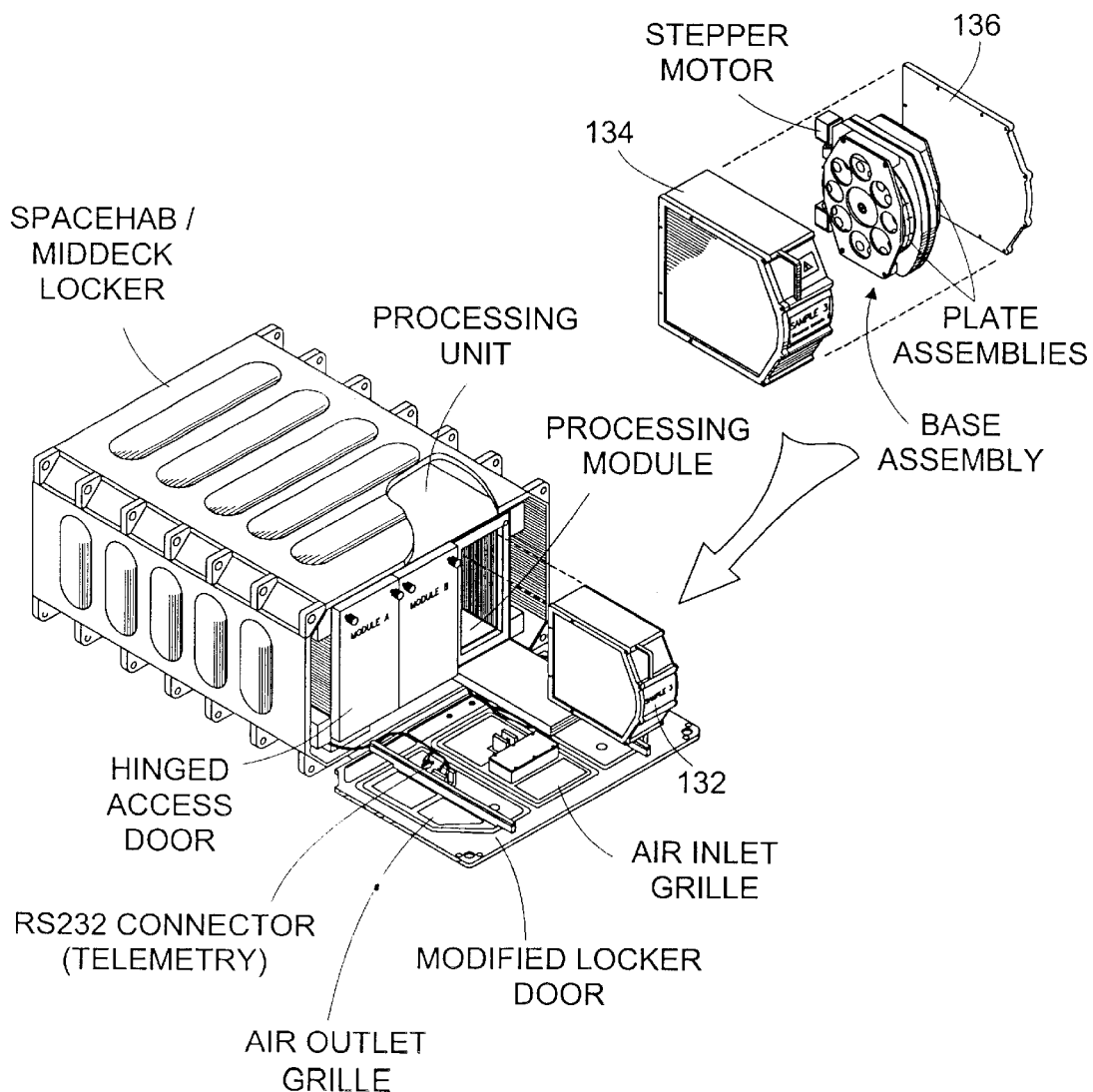
FIG. 20 is a perspective view showing a modular design of the processing unit providing a cassette change out.

FIG. 19 is an exploded perspective view showing an indexing system for MAGSEP for rotating the collection plate, wherein a tray cover 110 attaches to the plate assembly 100 which is connected to a worm gear 112 and providing an angular contact bearing 114 connected to a bearing standoff 116. The assembly is rotatively attached to a base assembly 119 having a bearing race relief 118, and position sensor 120, wherein the base 119 forms a tray 122 which is mechanical connection with shaft 124 of a precision worm 126 in communication with a flexible shaft coupling 128 driven be a stepper motor 130. The indexing system tray 58 is disposed within a cartridge or cassette 132 defined by a containment enclosure 134 and cover 136 holding the plate assembly as shown in FIG. 20 which is a perspective view showing a modular design of the processing unit providing a cassette change out.

Figure 21:
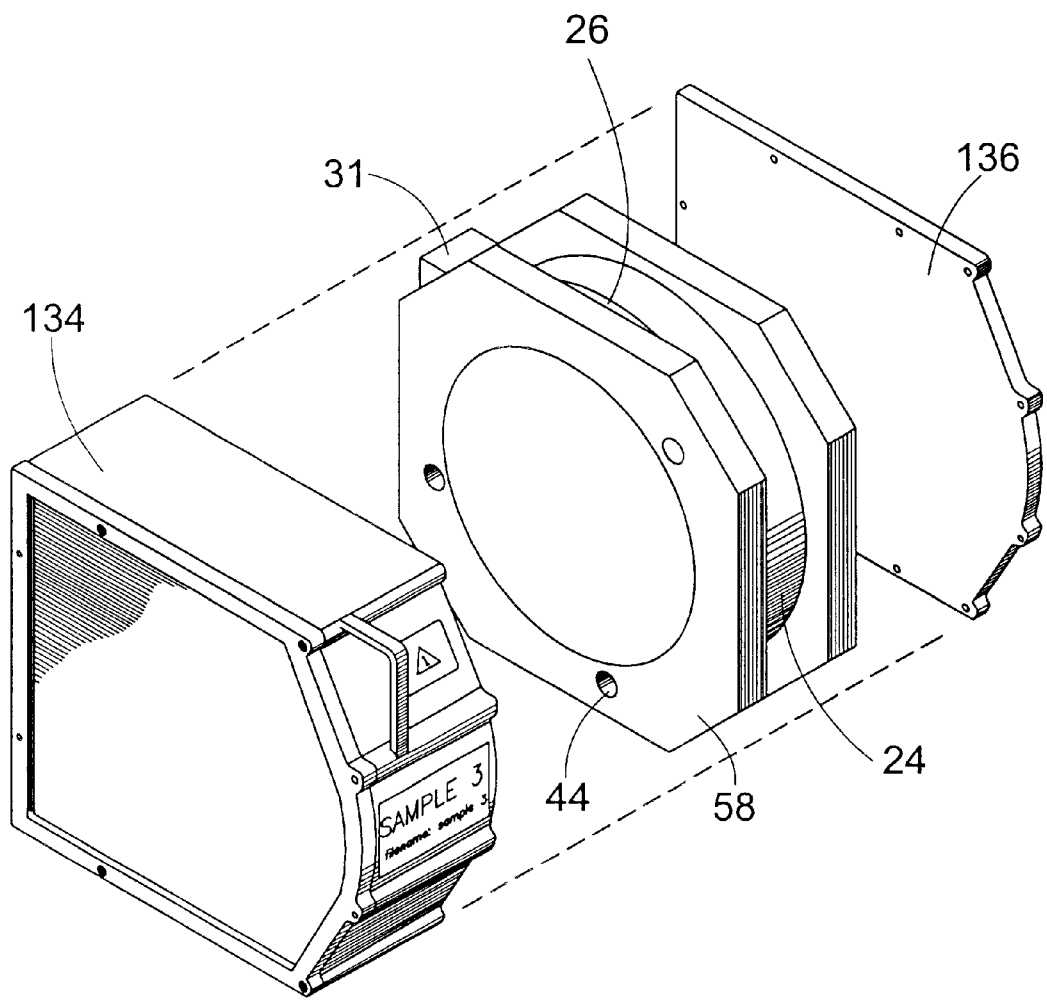
FIG. 21 is a perspective view showing a MAGSEP cassette occupying the same form factor as the space flight proven ADSEP cassette providing change out capabilities.

As shown in FIG. 21, a MAGSEP cassette can be utilized in a modular design including a processing module holding more of the same or different cassettes.

Figure 22:
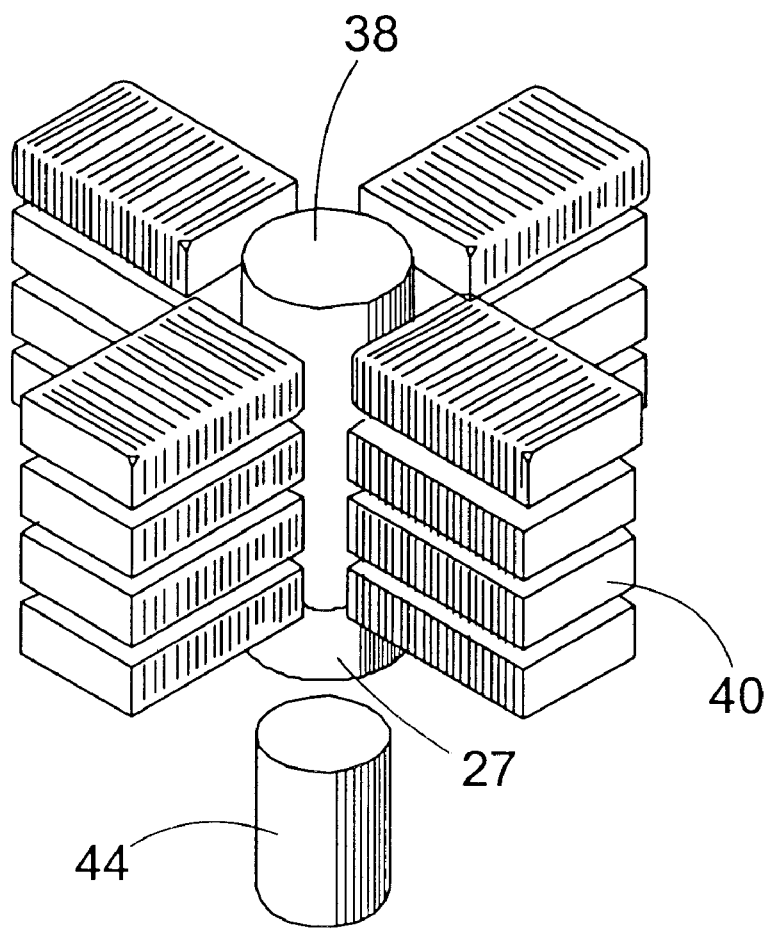
FIG. 22 is an alternate embodiment showing a translating magnet assembly utilizing multiple quadropole magnets energized sequentially in a cascading magnet design.

As an alternate embodiment, FIG. 22 shows the use of a cascading magnet system in which a series of dipole, quadrupole or ring magnets, say three or four, is stacked along the upper cylindrical cavity of the MAGSEP two-plate device. These are activated in sequence, lowest first, to accelerate (in the sense of a magnetic induction accelerator as used in particle physics) particles upward until they reach an unstable point as defined by Earnshaw's theorem, at which time the first field is switched off and the second switched on to continue the upward capture process without sticking the particles to the wall by magnetapheresis as set forth and described in U.S. Pat. No. 5,053,344 by Zborowski et al., 1995, hereby incorporated by reference.

FIG. 2 is this alternate embodiment showing a translating magnet assembly utilizing multiple quadropole magnets energized sequentially in a cascading magnet design consisting of a sample cuvette, separation electromagnet, collection cuvette, and holding electromagnet.

Figure 23:
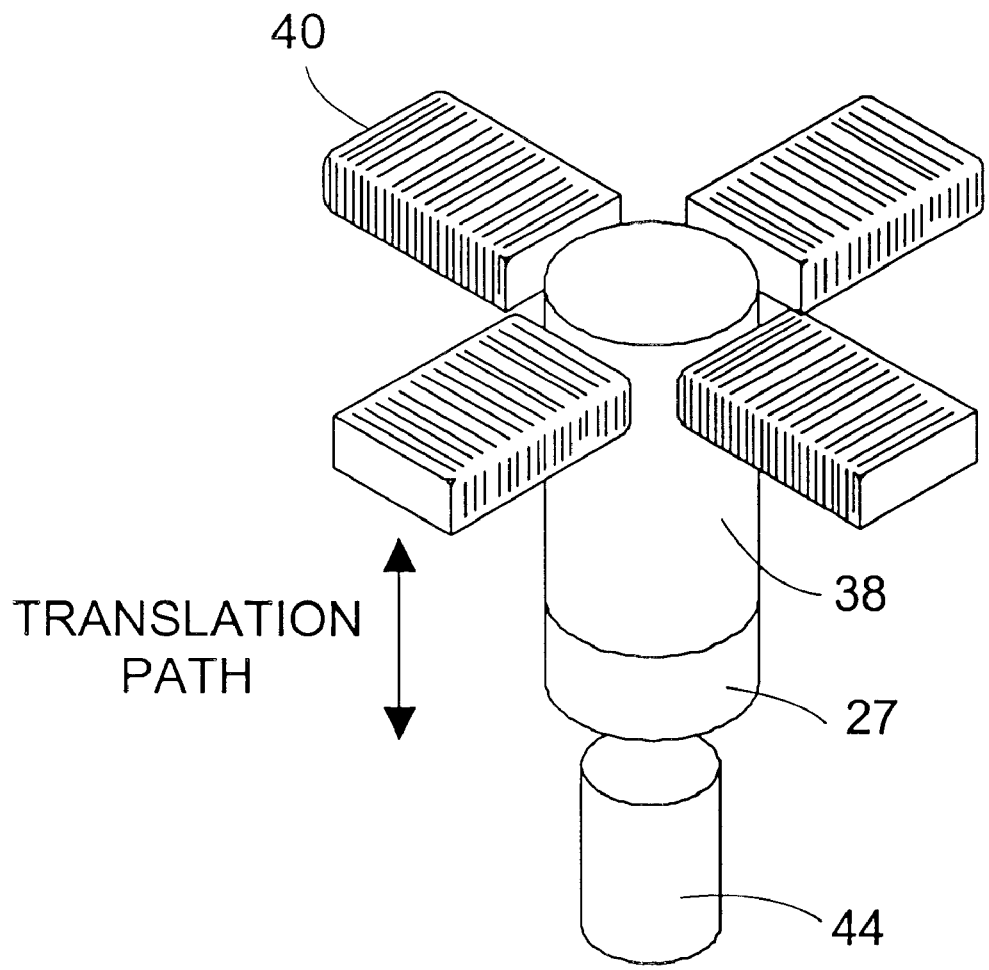
FIG. 23 is a an alternate embodiment showing a translating magnet assembly consisting of a moving quadruple magnet.

FIG. 23 is an alternate embodiment showing a translating magnet assembly consisting of a moving quadruple magnet consisting of a separation electromagnet, sample cuvette, collection cuvette, and holding electromagnet.

Figure 24:
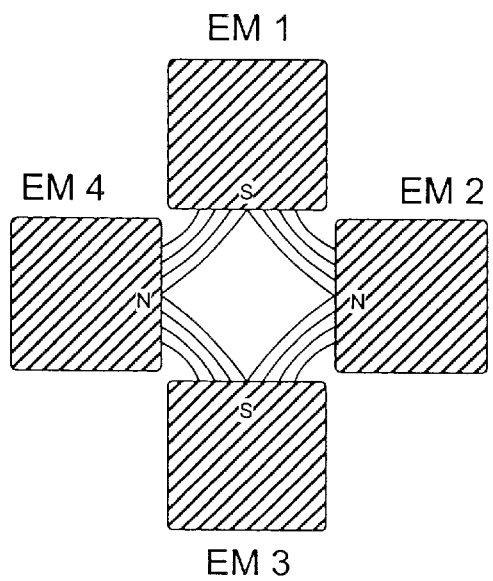
FIG. 24 is an alternate embodiment showing a quadruple or hexapole translating magnet.
Figure 24:
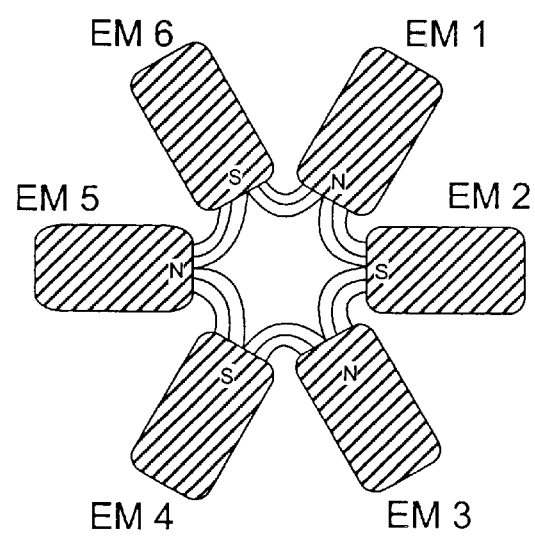

FIG. 24 is an alternate embodiment showing a quadruple or hexapole translating magnet.

Alternate Applications

The present invention could also be used as a means of "Magnetic Chromatography". Capture can be "isocratic", wherein magnets in all of the stages have equal strength, or "gradient" wherein magnets at increasing stage numbers have increasing field strength. In the latter case, in a typical application the first stage would have no magnet and no upper cavity and would serve the purpose of homogenizing the cell mixture by stirring just before the beginning of transfers. The second stage would have no magnet and would serve the purpose of adding magnetic particles to the cell suspension from a low volume upper cavity, mixing them together, and allowing them to react. The third stage would have a very weak magnet in the upper cavity, which would have similar volume to the lower cavity, and would attract only the most highly magnetized cells, namely those with the most receptors for the magnetic ligand. The fourth stage would have a stronger magnet than does the third in its upper compartment and would attract more weakly magnetized cells, etc. until, at the final-but-one stage the strongest magnet of all would capture the cells with the least receptors. The final stage would also have no magnet and would contain any remaining completely unmagnetized cells after the final transfer. In the presence of gravity uncaptured cells will settle into the lower cavities by gravitational sedimentation if the transfer times are made sufficiently long. In the absence of gravity uncaptured cells would remain in both the upper and lower cavities at each transfer; however, continued mixing with each transfer would have the effect of removing the uncaptured cells in each cavity.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplifications presented herein above. Rather, what is intended to be covered is within the spirit and scope of the appended claims.

We claim:

1. A method for quantitatively separating cells, proteins or other particles, and collecting at least some of said particles in a band using a multistage electromagnetic separator including a series of dipole, quadrupole or ring magnets, stacked along an upper cavity of an upper plate in rotational alignment with a lower plate including at least one sample container containing particles in a fluid in sealed fluid communication and cooperatively engaging said upper plate; comprising the steps of: activating at least one magnet providing a selection of field strengths in sequence, lowest field strength first, forming an electric field to accelerate said particles susceptible to said selected field strength upward until they reach an unstable point as defined by Earnshaw's theorem defining migrating particles, at which time a first field is switched off and a second field is switched on to continue the upward capture process without sticking said migrating particles to the wall by magnetophoresis.

2. A multistage electromagnetic separator for separating magnetically susceptible materials suspended in fluids, comprising:

a frame supporting a lower plate including at least one sample cuvette disposed therein containing at least one magnetic particle suspended in a fluid;

an upper plate in cooperative engagement with said lower plate, said upper plate including at least one collection cuvette disposed therein containing fluid alignable with said sample cuvette in said lower plate for fluid communication therewith;

a translating electromagnet energizable to a programmed current level translating from a bottom of said sample cuvette to the interface of said upper plate and said lower plate;

a holding electromagnet is energizable to a programmed current level for pulling said at least one magnetic particle within a specified mobility range into the top of said at least one collection cuvette;

means for rotating said upper plate with respect to said lower plate; and means for sealing said at least one magnetic particle within said at least one collection cuvette.

3. An electromagnetic separator for separating particles suspended in a fluid according to their magnetophoretic mobility, comprising:

a base unit including means for controlling, means for supporting, and means for providing electrical power to a plate rotation apparatus;

said plate rotation apparatus including a holding magnet, and a plate assembly;

said plate assembly comprising a first plate containing at least one collection cavity in selected fluid communication with and cooperatively engaging a second plate including at least one sample container holding said particles in said fluid disposed therein, said first plate moving with respect to said second plate;

means for moving said first plate with respect to said second plate;

means for aligning said first plate with respect to said second plate;

a translating magnet for generating an electric field;

means for controlling the movement of said first plate or said second plate, said translating electromagnet, and said holding magnet.

4. The electromagnetic separator of claim 3, wherein said holding magnet is selected from the group consisting of an electromagnet and a permanent magnet.

5. The electromagnetic separator of claim 3, wherein said first plate contains a plurality of collection cavities.

6. The electromagnetic separator of claim 3, wherein collection cavities comprise collection cuvettes.

7. The electromagnetic separator of claim 3, wherein said sample containers are sample cuvettes.

8. The electromagnetic separator of claim 3, wherein including a means for cooling said electromagnet.

9. The electromagnetic separator of claim 3, including means for rotating said first plate with respect to said second plate.

10. The electromagnetic separator of claim 3, wherein said first plate is an upper plate.

11. The electromagnetic separator of claim 3, wherein said second plate is a lower plate.

12. The electromagnetic separator of claim 3, including a holding magnet for each collection cavity.

13. The electromagnetic separator of claim 3, including an individual translational magnet for each sample.

14. The electromagnetic separator of claim 3, wherein said collection cavities and said holding magnets are arrayed in a geometric relationship.

15. The electromagnetic separator of claim 3, wherein said geometric relationship is linear.

16. The electromagnetic separator of claim 3, wherein said geometric relationship is circular.

17. The electromagnetic separator of claim 3, including a plurality of samples serving an array of said collection cavities.

18. The electromagnetic separator of claim 3, wherein said translating magnet comprises a series of fixed electromagnets of a selected polarity, operated in sequence so as to sweep said particles into a common starting band.

19. The electromagnetic separator of claim 3, wherein said sample is moved with respect to at least one stationary translating electromagnet of a selected polarity.

20. The electromagnetic separator of claim 3, wherein said translating magnet and said holding magnet is controlled by a computer.

21. The electromagnetic separator of claim 3, wherein said translating magnet comprises a single permanent or electromagnet forming a common starting band of particles at a selected position with said sample container.

22. The electromagnetic separator of claim 3, wherein said first plate includes a fill relief and vent port.

23. The electromagnetic separator of claim 3, wherein said first plate includes a sample vent port and fill port.

24. The electromagnetic separator of claim 3, wherein said translating magnet comprises a permanent dipole, a permanent quadrupole, a permanent hexapole magnet, a dipolar magnet, a quadrupolar electromagnet, or a circular electromagnet.

25. The electromagnetic separator of claim 3, wherein said translating magnet comprises a series of fixed electromagnets of any polarity, operated in sequence so as to sweep particles into a common starting band.

26. The electromagnetic separator of claim 3, wherein control of said translating magnet, said holding magnet, and said disk transfer system is controlled by a computer.

27. The electromagnetic separator of claim 3, wherein said collection cavities and said holding magnets are arrayed in a geometrical relationship of linear array.

28. The electromagnetic separator of claim 3, wherein said collection cavities and said holding magnets are arrayed in a geometrical relationship of a circle.

29. The electromagnetic separator of claim 3, wherein said at least one collection cavity is aligned using an analytical device.

30. The electromagnetic separator of claim 3, including means selected from the group consisting of a wax or grease for forming a seal between said first plate and said second plate.

31. An electromagnetic separator for separating particles suspended in a fluid according to their magnetophoretic mobility, comprising:

a base;

a holding magnet;

a first plate containing at least one collection cavity in selected fluid communication with and cooperatively engaging a second plate including at least one sample holding said particles in said fluid disposed therein, said first plate moving with respect to said second plate;

means for moving said first plate with respect to said second plate;

means for aligning said first plate with respect to said second plate;

means of electrical power;

means for controlling the movement of said first plate or said second plate and said holding electromagnet.

32. The electromagnetic separator of claim 31, including a translating electromagnetic.

33. The electromagnetic separator of claim 31, wherein said translating electromagnet.

34. The electromagnetic separator of claim 31, including means for sealing said first plate in fluid communication with said second plate.

35. The electromagnetic separator of claim 31, wherein said means for sealing comprises grease, wax, and lubricant.

36. The electromagnetic separator of claim 31, wherein a holding magnet stepper motor rotates said first plate.

37. The electromagnetic separator of claim 31, wherein said holding magnet is a 15× permanent magnet.

38. The electromagnetic separator of claim 31, wherein said holding magnet is a permanent magnet mounting on an arm connecting to a stepping motor, said stepping motor rotating said arm containing said holding magnet positioning said holding magnet with respect to said cavity.

39. The electromagnetic separator of claim 31, including an indexing system for rotating said first plate, said indexing system being disposed withing a cartridge.

40. The electromagnetic separator of claim 31, wherein said translational magnet includes translation rates range up to 420 micrometers per second.

41. The electromagnetic separator of claim 31, wherein said translational magnet includes translation rates range down to 5 micrometers per second.

42. The electromagnetic separator of claim 31, wherein said translation magnet has a field strength programmable in a range of from 0 to 1400 gauss measured at the poleface.

43. An electromagnetic separator for separating magnetically susceptible materials suspended in fluids, comprising:
a frame supporting a lower plate including at least one sample container disposed therein containing at least one magnetic particle suspended in a fluid;
an upper plate in cooperative engagement with said lower plate, said upper plate including at least one collection cavity disposed therein containing fluid alignable with said sample container in said lower plate for fluid communication therewith;
a translating electromagnet energizable to a programmed current level translating from a selected point of said sample container to a selected position below the interface of said upper plate and said lower plate;
a holding electromagnet is energizable to a programmed current level for pulling said at least one magnetic particle within a specified mobility range into the top of said at least one collection cavity;
means for rotating said upper plate with respect to said lower plate; and
means for sealing said at least one magnetic particle within said at least one collection cuvette.

44. A method of collecting a particle sample with a plate assembly, comprising the steps of:
cooperatively engaging a first plate with a second plate, said second plate including at least one opening therein, said second plate cooperatively engaging said first plate and forming a seal thereinbetween;
disposing at least one particle in at least one sample container, said sample container being in fluid communication with said at least one opening;
rotating and aligning said opening in said second plate and said at least one sample container with said collection cavity in said first plate;
transferring said at least one particle in said sample container into said collection cuvette; and
rotating said second plate and said sample container with respect to said first plate and said collection cuvette capturing said at least one particle within said collection cuvette of said first plate.

45. A method for quantitatively separating particles with a multistage electromagnetic separator, comprising the steps of:
activating in sequence a series of magnets comprising at least a first magnet and a second magnet stacked along a cavity of multiplate separator having at least a first plate and a second plate in cooperative engagement with one another;
creating a first magnetic field with said first magnet and a second magnetic field with said second magnet;
accelerating said particles until said particles reach an unstable point;
switching off said first magnet and said first magnetic field;
switching on said second magnet and said second magnetic field moving said particles to a selected point without sticking said particles to a wall of said cavity;
separating said particles based on its magnetophoretic mobility; and
capturing said particles.

46. The method for quantitatively separating particles with a multistage electromagnetic separator of claim 45, including the step of achieving multi-stage separation by utilizing multiple cavities with said plate.

47. The method for quantitatively separating particles with a multistage electromagnetic separator of claim 45, including the step of varying the field strength of said translating magnet during said separation process.

48. The method for quantitatively separating particles with a multistage electromagnetic separator of claim 45, including the step of suspending said holding magnet over said cavity.

49. The method for quantitatively separating particles with a multistage electromagnetic separator of claim 45, including the step of varying the field strength of said holding magnet during said separation process.

50. The method for quantitatively separating particles with a multistage electromagnetic separator of claim 45, including the step of using a step-wise rotary distribution and containment system for selecting, isolating, and storing particles of different magnetophoretic mobilities.

51. The method for quantitatively separating particles with a multistage electromagnetic separator of claim 45, including the step of each stage containing a magnetophoretic mobility cutoff based on the magnetic field strength of the collection magnet and the dwell time of the collection.

52. The method for quantitatively separating particles with a multistage electromagnetic separator of claim 45, wherein said particles comprise cells, proteins, enzymes, chemicals, ligands, lectins, and combinations thereof.

53. The method for quantitatively separating particles with a multistage electromagnetic separator of claim 45, wherein said cavity is a cylindrical cavity.

54. The method for quantitatively separating particles with a multistage electromagnetic separator of claim 45, wherein said magnet is selected from the group consisting of at least one dipole magnet, at least one quadruppole magnet, at least one hexapole magnet, at least one circular electromagnet, at least one permanent dipole magnet, at least one permanent quadrupole magnet, at least one permanent hexapole magnet, and combinations thereof.

55. The method for quantitatively separating particles with a multistage electromagnetic separator of claim 45, wherein said first magnet comprises a series of fixed electromagnets of any polarity, operated in sequence so as to sweep particles into a common starting band.

56. The method for quantitatively separating particles with a multistage electromagnetic separator of claim 45, wherein said translating electromagnet moves up and down said sample container.

57. The method for quantitatively separating particles with a multistage electromagnetic separator of claim 45, wherein said particles are contained in a sample cuvette.

58. The method for quantitatively separating particles with a multistage electromagnetic separator of claim 45, wherein said particles emerge from said sample container at a velocity that is proportional to magnetophoretic mobility and magnetic susceptibility.

59. The method for quantitatively separating particles with a multistage electromagnetic separator of claim 45, including the step of labeling said particles with liganded magnetic particles and separating said particles by its receptor density.

60. The method for quantitatively separating particles with a multistage electromagnetic separator of claim 45, wherein said particles are suspended in a solution.

61. The method for quantitatively separating particles with a multistage electromagnetic separator of claim 45, including the step of stratifying in layers said particles within said sample container into fast particles, magnetized particles, slow particles, and sedimenting non-magnetic particles.

62. The method for quantitatively separating particles with a multistage electromagnetic separator of claim 45, including the step of removing said layers of said stratified particles into individual collection cavities.

63. The method for quantitatively separating particles with a multistage electromagnetic separator of claim 45, including the step of isolating mixtures of combinatorially synthesized molecules into groups of products according to its physical and/or chemical properties.

64. The method for quantitatively separating particles with a multistage electromagnetic separator of claim 45, wherein said chemical and/or physical properties comprises its size, length, shape, molecular weight, and structural elements.

65. The method for quantitatively separating particles with a multistage electromagnetic separator of claim 45, including the step of analyzing said particles for the ability to bind specifically to an antibody, receptor, or the ligate.

66. The method for quantitatively separating particles with a multistage electromagnetic separator of claim 45, including the step of collecting said analyzed particles forming a ligand library containing a greater number of conformations available to any one sequence for studying molecular recognition.

67. The method for quantitatively separating particles with a multistage electromagnetic separator of claim 45, including the step of combining ligand libraries forming combinational chemical libraries containing known and random sequences and surveying said libraries for strong ligands and recognizing and isolating agonists, antagonists, enzyme inhibitors, virus blockers, antigens, pharmaceuticals, and combinations thereof.

68. The method for quantitatively separating particles with a multistage electromagnetic separator of claim 45, including the step of separating said particles according to their magnetic strength by rate.

69. The method for quantitatively separating particles with a multistage electromagnetic separator of claim 45, including the step of separating said particles according to their magnetic strength by an equilibrium process.

70. The method for quantitatively separating particles with a multistage electromagnetic separator of claim 45, including the step of decanting contaminant suspensions of unwanted particles by leaving them in the sample container as by-products of the process.

71. The method for quantitatively separating particles with a multistage electromagnetic separator of claim 45, wherein said sample is contained in a cuvette.

72. The method for quantitatively separating particles with a multistage electromagnetic separator of claim 45, including the step of making only one buffer for completing collection of said particles.

73. The method for quantitatively separating particles with a multistage electromagnetic separator of claim 45, including the step of collecting said particles in separated fractions.

74. The method for quantitatively separating particles with a multistage electromagnetic separator of claim 45, including the step selecting particles comprising cells, enzymes, and lectins having specific carbohydrate recognition sites, conjugating a specific carbohydrate on a surface of a magnetic bead of a selected magnetic strength forming a glycoconjugate, and separating from a mixed population particles that recognize a first glycoconjugate on a strongly magnetizable bead from particles that recognize a second glycoconjugate on a weakly magnetizable bead.

75. The method for quantitatively separating particles with a multistage electromagnetic separator of claim 45, including the step of differential separation n the basis of small differences in surface composition of said particle.

76. The method for quantitatively separating particles with a multistage electromagnetic separator of claim 45, including the step of using countercurrent extraction to separate particles quantitatively on the basis of the number of ligands bound to particles of the same type some with high receptor content and some with low receptor content.

77. The method for quantitatively separating particles with a multistage electromagnetic separator of claim 45, including the step of using countercurrent extraction to separate particles qualitatively based on the amount of ligand bound to each kind of particle.

78. The method for quantitatively separating particles with a multistage electromagnetic separator of claim 45, including the step of sorting particles comprising cell components of plants and animals.

79. The method for quantitatively separating particles with a multistage electromagnetic separator of claim 45, wherein said magnetic field has a variable field strength.

80. The method for quantitatively separating particles with a multistage electromagnetic separator of claim 45, wherein said magnetic field has a variable field strength of up to 1000 mT.

81. The method for quantitatively separating particles with a multistage electromagnetic separator of claim 45, including the step of positioning said first plate with respect to said second plate by an indexing system for plate translation.

82. The method for quantitatively separating particles with a multistage electromagnetic separator of claim 45, including the step of configuring said method for insertion into an ADSEP containment enclosure for space flight and remote applications.

83. The method for quantitatively separating particles with a multistage electromagnetic separator of claim 45, including the step of incorporating data management and a processing control system therewith.

84. The method for quantitatively separating particles with a multistage electromagnetic separator of claim 45, wherein said first magnet is an electromagnet having a relatively quick change in polarity to enhance mixing.

85. The method for quantitatively separating particles with a multistage electromagnetic separator of claim 45, including the step of creating a constant force and a formed flux density.

86. The method for quantitatively separating particles with a multistage electromagnetic separator of claim 45, including the step of selecting particles comprising biological cells that hove on their surfaces receptors that can be bound by an antibody attached to magnetic particles through a specific chemical ligand that can be chemically bound to the antibody thereby attaching said biological cells to magnetic particles for collection.

87. The method for quantitatively separating particles with a multistage electromagnetic separator of claim 45, including the step of selecting particles having homogeneous populations of magnetic particles from heterogeneous magnetic particles synthesized for use in cell research applications.

88. The method for quantitatively separating particles with a multistage electromagnetic separator of claim 45, including the step of selecting strong, homogeneous populations of magnetic particles from targeted drug delivery whereby magnetic microparticles are used for the parenteral delivery of targeted drugs based wherein the differentiation and selection thereof is due to the fact that magnetically weak particles are inimical to the modality.

89. The method for quantitatively separating particles with a multistage electromagnetic separator of claim 45, including the step of separating magnetically labeled biological cells.

90. The method for quantitatively separating particles with a multistage electromagnetic separator of claim 45, including the step of labeling biological substrates with decreasing numbers of paramagnetic beads and separating quantitatively said substrates on the basis of the extent of labeling by using magnetic fields of increasing strength.

91. The method for quantitatively separating particles with a multistage electromagnetic separator of claim 45, including the step of labeling biological substrates with decreasing numbers of paramagnetic beads and separating quantitatively said substrates on the basis of the extent of labeling and the dwell time of the collection.

92. The method for quantitatively separating particles with a multistage electromagnetic separator of claim 45, including the step of selecting homogeneous populations of magnetic microparticles for application to cell separation and biochemical separation processes.

93. The method for quantitatively separating particles with a multistage electromagnetic separator of claim 45, including the step of selecting homogeneous subpopulations of magnetic particles for targeted drug delivery.

94. The method for quantitatively separating particles with a multistage electromagnetic separator of claim 45, including the step of classifying separation of magnetic particle according to magnetophoretic mobility and hence volumetric differential susceptibility.

95. A method for quantitatively separating particles with a multistage electromagnetic separator for separating particles suspended in a fluid according to their magnetophoretic mobility, comprising a base unit including means for controlling, means for supporting, and means for providing electrical power to a plate rotation apparatus, said plate rotation apparatus including a translating electromagnet, an electromagnetic holding magnet, a permanent holding magnet, and a plate assembly including an upper plate containing at least one collection cavity in selected fluid communication with and cooperatively engaging a second plate including at least one sample container holding said particles in said fluid disposed therein, said first plate moving with respect to said second plate, means for moving said first plate with respect to said second plate, means for aligning said first plate with respect to said second plate, and means for controlling the movement of said first plate or said second plate, said translating electromagnet, and said holding magnet, comprising the steps of:

filling said at least one sample container through a sample port in said upper plate with a solution containing at least some magnetic particles;

rotating said upper plate to a full step position aligning said at least one collection cavity of said upper plate with said at least one sample container of said lower plate;

activating said translation magnet energizing and moving said particles toward said lower plate and said upper plate interface;

de-energizing said translating magnet;

energizing said holding electromagnet;

coupling holding electromagnetic field with a magnetic field of said permanent holding magnet;

de-energizing said holding electromagnet;

rotating said upper plate capturing a selected fraction of said particles in a selected collection cavity.

96. The method for quantitatively separating particles with a multistage electromagnetic separator of claim 95, wherein a sample container and its translating magnet serves an array of collection cavities.

97. The method for quantitatively separating particles with a multistage electromagnetic separator of claim 95, including the step of labeling said particles with decreasing numbers of paramagnetic beads.

98. The method for quantitatively separating particles with a multistage electromagnetic separator of claim 95, including the step of separating said paramagnetic beads quantitatively on the basis of the extent of labeling by using magnetic fields of increasing strength.

99. A method for quantitatively separating particles with a multistage electromagnetic separator for separating particles suspended in a fluid according to their magnetophoretic mobility, comprising a base unit including means for controlling, means for supporting, and means for providing electrical power to a plate rotation apparatus, said plate rotation apparatus including a translating electromagnet, an electromagnetic holding magnet, a permanent holding magnet, and a plate assembly including an upper plate containing at least one collection cavity in selected fluid communication with and cooperatively engaging a second plate including at least one sample container holding said particles in said fluid disposed therein, said first plate moving with respect to said second plate, means for moving said first plate with respect to said second plate, means for aligning said first plate with respect to said second plate, and means for controlling the movement of said second plate with respect to said second plate, said translating electromagnet, and said holding magnet, comprising the steps of:

half stepping rotation of said upper plate;

filling said at least one collection cavity and at least one sample container with fluid samples;

rotating and aligning said at least one upper collection cavity into position above said at least one sample container;

energizing said translating electromagnet to a programmed current level creating a magnetic field within said at least one sample container, subjecting said particles thereto, and attracting at least one particle with a specified mobility range;

de-energizing said translational magnet;

energizing said holding electromagnet to a programmed current level pulling said at least one particle within a specified mobility range into said at least one collection cavity;

de-energizing said holding electromagnet;

holding said at least one particle within a specified mobility range in position within said collection cavity with said holding magnet; and rotating said upper plate thereby capturing said at least one particle within a specified mobility range.

100. The method for quantitatively separating particles with a multistage electromagnetic separator for separating particles of claim 99, including the step of translating said translating electromagnet from a bottom of said at least one sample container to an interface of said upper plate and said lower plate.

101. The method for quantitatively separating particles with a multistage electromagnetic separator for separating particles of claim 99, including the step of translating said translating electromagnet from a selected position along said at least one sample container to another selected position along said at least one sample container.

102. The method for quantitatively separating particles with a multistage electromagnetic separator for separating particles of claim 99, including the step of moving said at least one sample container within an electric field produced by said translating electromagnet.

103. The method for quantitatively separating particles with a multistage electromagnetic separator for separating particles of claim 99, including the step of sequentially energizing a at least two translating magnets positioned from a bottom of said sample container to a top of said sample container creating a magnetic field of different current levels.

104. The method for quantitatively separating particles with a multistage electromagnetic separator for separating particles of claim 99, including the step of sequentially energizing a at least two translating magnets positioned from a bottom of said sample container to a top of said sample container creating a magnetic field of different current levels.

105. The method for quantitatively separating particles with a multistage electromagnetic separator for separating particles of claim 99 wherein said holding magnet is selected from a group of permanent magnets comprising different sizes and materials.

106. The method for quantitatively separating particles with a multistage electromagnetic separator for separating particles of claim 99 including the step of suspending said particles in a solution of water, polyethylene glycol, alcohol, and combinations thereof.

107. The method for quantitatively separating particles with a multistage electromagnetic separator for separating particles of claim 99, including the step of using an index system to rotate said upper plate.

108. The method of claim 1, including the step of:

collecting said particles in a band by moving said magnet having a gap, from a bottom of said at least one sample container to a selected different position;

forming said electric field by translating said electromagnet upward carrying said migrating particles in the path of the gap;

switching off said electromagnet upon said migrating particles reaching a predetermined level forming a band of migrating particles;

activating a holding magnet positioned above said cavity causing said migrating particles in said band within said sample container to migrate upward at a velocity proportional to their volumetric magnetic susceptibility;

collecting said migrating particles in said collection cavity of said upper plate;

rotating said upper plate and said collection cavity containing said migrating particles sealing said collection cavity; and aligning a second collection cavity in fluid communication with said sample container and repeating said process to quantitatively and qualitatively separate said particles contained in said sample container in accordance with their magnetic susceptibility.

* * * * *